United States Patent
Chidambaran et al.

(10) Patent No.: US 12,146,193 B2
(45) Date of Patent: *Nov. 19, 2024

(54) METHODS AND COMPOSITIONS RELATING TO OPRM1 DNA METHYLATION FOR PERSONALIZED PAIN MANAGEMENT

(71) Applicant: Children's Hospital Medical Center, Cincinnati, OH (US)

(72) Inventors: Vidya Chidambaran, Cincinnati, OH (US); Senthilkumar Sadhasivam, Mason, OH (US); Hong Ji, Cincinnati, OH (US); Lisa Martin, West Chester, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/179,607

(22) Filed: Mar. 7, 2023

(65) Prior Publication Data

US 2023/0265518 A1    Aug. 24, 2023

Related U.S. Application Data

(63) Continuation of application No. 16/478,706, filed as application No. PCT/US2018/014405 on Jan. 19, 2018, now Pat. No. 11,618,924.

(60) Provisional application No. 62/448,540, filed on Jan. 20, 2017.

(51) Int. Cl.
*C12Q 1/6883*    (2018.01)

(52) U.S. Cl.
CPC ..... *C12Q 1/6883* (2013.01); *C12Q 2600/106* (2013.01); *C12Q 2600/154* (2013.01)

(58) Field of Classification Search
CPC ............ C12Q 1/6883; C12Q 2600/106; C12Q 2600/154
USPC .......................................................... 514/49
See application file for complete search history.

(56) References Cited

U.S. PATENT DOCUMENTS

| | | |
|---|---|---|
| 4,376,110 A | 3/1983 | David et al. |
| 4,675,904 A | 6/1987 | Silverman |
| 5,148,483 A | 9/1992 | Silverman |
| 5,288,644 A | 2/1994 | Beavis et al. |
| 5,445,934 A | 8/1995 | Fodor et al. |
| 5,700,637 A | 12/1997 | Southern |
| 5,744,305 A | 4/1998 | Fodor et al. |
| 5,945,334 A | 8/1999 | Besemer et al. |
| 5,976,081 A | 11/1999 | Silverman |
| 6,054,270 A | 4/2000 | Southern |
| 6,300,063 B1 | 10/2001 | Lipshutz et al. |
| 6,429,027 B1 | 8/2002 | Chee et al. |
| 6,733,977 B2 | 5/2004 | Besemer et al. |
| 6,858,394 B1 | 2/2005 | Chee et al. |
| 7,364,858 B2 | 4/2008 | Barany et al. |
| 7,754,428 B2 | 7/2010 | Lo |
| 7,858,313 B2 | 12/2010 | Ikeda et al. |
| 9,691,411 B2 | 6/2017 | Scherer et al. |
| 9,944,985 B2 | 4/2018 | Sadhasivam et al. |
| 10,662,476 B2 | 5/2020 | Sadhasivam et al. |
| 10,878,939 B2 | 12/2020 | Sadhasivam |
| 11,618,924 B2 * | 4/2023 | Chidambaran ...... C12Q 1/6883 514/49 |
| 2002/0077825 A1 | 6/2002 | Silverman et al. |
| 2002/0110823 A1 | 8/2002 | Szuster |
| 2003/0078768 A1 | 4/2003 | Silverman et al. |
| 2003/0092019 A1 | 5/2003 | Meyer et al. |
| 2003/0167189 A1 | 9/2003 | Lutgen et al. |
| 2007/0233468 A1 | 10/2007 | Ozdas et al. |
| 2007/0233498 A1 | 10/2007 | Silverman et al. |
| 2008/0201280 A1 | 8/2008 | Martin et al. |
| 2009/0253585 A1 | 10/2009 | Diatchenko et al. |
| 2010/0143929 A1 | 6/2010 | Levenson |
| 2010/0240552 A1 | 9/2010 | Ikeda et al. |
| 2010/0262603 A1 | 10/2010 | Odom et al. |
| 2011/0257098 A1 | 10/2011 | Tueffard et al. |
| 2012/0041911 A1 | 2/2012 | Pestian et al. |
| 2012/0283117 A1 | 11/2012 | Rothenberg |
| 2012/0288068 A1 | 11/2012 | Jaiswal et al. |
| 2013/0035961 A1 | 2/2013 | Yegnanarayanan |
| 2013/0310549 A1 | 11/2013 | Shuber |
| 2014/0371256 A1 | 12/2014 | Sadhasivam et al. |
| 2016/0180041 A1 | 6/2016 | Pestian et al. |
| 2017/0061073 A1 | 3/2017 | Sadhasivam |
| 2017/0233813 A1 | 8/2017 | Rothenberg et al. |
| 2018/0334717 A1 | 11/2018 | Sadhasivam et al. |

(Continued)

FOREIGN PATENT DOCUMENTS

| | | |
|---|---|---|
| EP | 0619321 A1 | 10/1994 |
| EP | 0619321 B1 | 1/1999 |

(Continued)

OTHER PUBLICATIONS

Glossary of medical education terms, Institute of International Medical Education. http://www.iime.org/glossary.htm Accessed in Mar. 2013. (Year: 2013).*
Berde et al. "Comparison of morphone and methadone for prevention of postoperative pain in 3-7 year old children" Journal of Pediatrics, vol. 119, No. 1, Part 1, 1991.
Buchheit et al., Epigenetics and the Transition from Acute to Chronic Pain. Pain Medicine. 2012, vol. 13, No. 11, pp. 1474-1490.

(Continued)

*Primary Examiner* — Yih-Horng Shiao
(74) *Attorney, Agent, or Firm* — KDW Firm PLLC

(57) ABSTRACT

The disclosure relates to methods for pain management in the perioperative context, particularly through the use of the DNA methylation status of the human OPRM1 gene as a biomarker for increased susceptibility to perioperative pain, and related methods and compositions.

21 Claims, 3 Drawing Sheets

Specification includes a Sequence Listing.

(56) References Cited

U.S. PATENT DOCUMENTS

| | | |
|---|---|---|
| 2020/0308648 A1 | 10/2020 | Sadhasivam et al. |
| 2020/0318194 A1 | 10/2020 | Sadhasivam et al. |
| 2020/0340061 A1 | 10/2020 | Sadhasivam et al. |
| 2021/0205346 A1 | 9/2021 | Chidambaran et al. |

FOREIGN PATENT DOCUMENTS

| | | |
|---|---|---|
| EP | 2785874 B1 | 9/2018 |
| JP | 2012070732 A | 4/2012 |
| WO | 8910977 A1 | 11/1989 |
| WO | 03054166 A2 | 7/2003 |
| WO | 03054166 A3 | 3/2004 |
| WO | 2005095601 A2 | 10/2005 |
| WO | 2005105093 A2 | 11/2005 |
| WO | 2005105093 A3 | 9/2006 |
| WO | 2009067473 A2 | 5/2009 |
| WO | 2010126867 A1 | 11/2010 |
| WO | 2012025765 A1 | 3/2012 |
| WO | 2012177945 A2 | 12/2012 |
| WO | 2012177945 A3 | 2/2013 |
| WO | 2013082308 A1 | 6/2013 |
| WO | 2013126834 A1 | 8/2013 |
| WO | 2013155010 A1 | 10/2013 |
| WO | 2014059178 A1 | 4/2014 |
| WO | 2014190269 A1 | 11/2014 |
| WO | 2015017731 A1 | 2/2015 |
| WO | 2015127379 A1 | 8/2015 |
| WO | 2016023026 A1 | 2/2016 |
| WO | 2018136728 A1 | 7/2018 |
| WO | 2020006175 A1 | 1/2020 |

OTHER PUBLICATIONS

Chorbov et al, Elevated Levels of DNA Methylation At the OPRM1 Promoter in Blood and Sperm From Male Opioid Addicts. Journal of Opioid Management. 2011, vol. 7, No. 4; pp. 1-11.
International Search Report and Written Opinion mailed on May 10, 2018 for International Application No. PCT/US2018/014405, filed Jan. 19, 2018.
Kesimci et al. "Association between ABCB1 gene polymorphisms and fentanyl's adverse effects in Turkish patients undergoing spinal anesthesia" Gene 493 (2012) 273-277.
Perwitasari, Dyah Aryani., "Polymorphisms of organic cation transporter 1 and the drugs response" J. Med. Sci. vol. 43, No. 2, Jun. 2011: 138-144.
Shipton, E A. "Tramadol—present and future." Anaesthesia and intensive care vol. 28,4 (2000): 363-74.
Tzvetkov, M V et al. "Genetically polymorphic OCT1: another piece in the puzzle of the variable pharmacokinetics and pharmacodynamics of the opioidergic drug tramadol." Clinical pharmacology and therapeutics vol. 90,1 (2011): 143-50.
Tzvetkov, M. et al. "Morphine is a Substrate of the Organic Cation Transporter OCT1 and Polymorphisms in the OCT1 Gene Affect Morphine Pharmacokinetics. M. V." Clin. Pharmacol. Ther. 91:S105(2012). [abstract].
Bedini, et al. (2008). "Transcriptional Activation of Human mu-opioid Receptor Gene by Insulin-like Growth Factor-I in Neuronal Cells is Modulated by the Transcription Factor REST." Journal of Neurochemistry 105(6):2166-2178.
Chidambaran, et al. (2017). "DNA Methylation at the mu-I Opioid Receptor Gene (OPRM I) Promoter Predicts Preoperative, Acute, and Chronic Postsurgical Pain After Spine Fusion." Pharmacogenomics and Personalized Medicine 10:157-168.
Doehring, et al. (2013). "Chronic Opioid Use is Associated with Increased DNA Methylation Correlating with Increased Clinical Pain." Pain 154(1):15-23.
Knothe, et al. (2016). "Pharmacoepigenetics of the Role of DNA Methylation in μ-opioid Receptor Expression in Different Human Brain Regions." Epigenetics 8(12):1583-1599.
Sun, et al. (Nov. 4, 2015). "DNA Methylation Modulates Nociceptive Sensitization after Incision." PloS One 10(11):1-16.
Viet, et al. (Jun. 24, 2014). "Demethylating Drugs as Novel Analgesics for Cancer Pain." Clinical Cancer Research 20(18):4882-4893.
Viet, et al. (Sep. 2017). "OPRM1 Methylation Contributes to Opioid Tolerance in Cancer Patients." The Journal of Pain 18(9):1046-1059.
Zhou, et al. (2014). "Increased Methylation of the RIOR Gene Proximal Promoter in Primary Sensory Neurons Plays a Crucial Role in the Decreased Analgesic Effect of Opioids in Neuropathic Pain." Molecular Pain 10(1):51-64.
Extended European Search Report mailed on Oct. 28, 2020 for EP Application No. 18741087.3, filed Jan. 19, 2018 in the International Application No. PCT/US2018/014405. 9 pages.
International Preliminary Report received for PCT International Application No. PCT/US2019/039411, mailed date Jan. 7, 2021, 7 pages.
GABA Receptor, Wikipedia 12 pages, Nov. 25, 2021.
Partial European Search Report dated Feb. 28, 2022 from International Patent Application No. 19826435.0, Mailed on Feb. 28, 2022; 4 pages.
Lirk, et al. Epigenetics in the Perioperative Period, British Journal of Pharmacology 172(11):2748-55, Jun. 2015.
Mauck, et al. Epigenetics of Chronic Pain after Thoracic Surgery, Current Opinion in Anaesthesiology 27(1):1-5., Feb. 2014.
Stephens, et al. Associations Between Genetic and Epigenetic Variations in Cytokine Genes and Mild Persistent Breast Pain in Women Following Breast Cancer Surgery, Cytokine 99:203-213, Nov. 2017.
Si et al., Correlations Between Inflammatory Cytokines, Muscle Damage Markers and Acute Postoperative Pain Following Primary Total Knee Arthroplasty, BMC Musculoskeletal Disorders, 18(1):265, Jun. 17, 2017.
Anderson, et al. (Sep. 2011). "Evaluation of a morphine maturation model for the prediction of morphine clearance in children." British Journal of Clinical Pharmacology 72(3):518-520.
Anonymous, (Apr. 24, 2018). "Ilumina technical bulletin" titled: "Top/Bot Strand and "A/B" allele." 3 pages.
Barratt, et al. (Apr. 18, 2012). "ABCB1 haplotype and OPRM1 118A>G genotype interaction in methadone maintenance treatment pharmacogenetics." Pharmacogenomics and Personalized Medicine 5(1):53-62.
Biesiada, et al. (Nov. 2014). "Genetic risk signatures of opioid-induced respiratory depression following pediatric tonsillectomy." Pharmacogenomics 15(14):1749-1762.
Branford, et al. (Jul. 27, 2012). "Opioid genetics: the key to personalized pain control?" Clinical Genetics 32(4):301-310.
Campa, et al. (Sep. 26, 2007). "Association of ABCB1/MDR1 and OPRM1 gene polymorphisms with morphine pain relief." Clinical Pharmacology & Therapeutics 83(4):559-566.
Chang, et al. (Apr. 8, 2010). "SNP-RFLPing 2: an updated and integrated PCR-RFLP tool for SNP genotyping." BMC Bioinformatics 11(1). 7 pages.
Chidambaran, et al. (Mar. 2017). "ABCC3 Genetic Variants Are Associated With Postoperative Morphine-Induced Respiratorydepression And Morphine Pharmacokinetics In Children." Pharmacogenomics Journal 17(2): 162-169.
Choi, et al. (Oct. 2010). "Association of ABCB1 polymorphisms with the efficacy of ondansetron for postoperative nausea and vomiting." Anaesthesia 65(10):996-1000.
Clavijo, et al. (Mar. 12, 2011). "A sensitive assay for the quantification of morphine and its active metabolites in human plasma and dried blood spots using high-performance liquid chromatography-tandem mass spectrometry." Analytical and Bioanalytical Chemistry 400(3):715-728.
Cohen, et al. (Aug. 2012). "Pharmacogenetics in perioperative medicine." Current opinion in anaesthesiology 25 (4):419-427.
Collins, et al. (Oct. 2005). "Online Selection of Discriminative Tracking Features." IEEE Transactions on Pattern Analysis and Machine Intelligence 27(10):1631-1643.
Coulbault, et al. (Apr. 1, 2006). "Environmental and genetic factors associated with morphine response in the postoperative period." Clinical Pharmacology & Therapeutics 79(4):316-324.

(56) References Cited

OTHER PUBLICATIONS

Crews, et al. (Jan. 29, 2014). "Clinical Pharmacogenetics Implementation Consortium Guidelines For Cytochrome P450 2d6 Genotype And Codeine Therapy." Clinical Pharmacology & Therapeutics 95(4):376-382.
De Gregori, et al. (Nov. 1, 2010). "Individualizing pain therapy with opioids: The rational approach based on pharmacogenetics and pharmacokinetics." European Journal of Pain Supplements 4(4):245-250.
Dellon, et al. (Oct. 22, 2013). "Clinical and endoscopic characteristics do not reliably differentiate PPI-responsive esophageal eosinophilia and eosinophilic esophagitis in patients undergoing upper endoscopy: a prospective cohort study." The American Journal of Gastroenterology 108(12):1854-1860.
Dellon, et al. (May 1, 2014). "59 Immunohistochemical Evidence of Inflammation Is Similar in Patients with Eosinophilic Esophagitis and PPI-Responsive Esophageal Eosinophilia: A Prospective Cohort Study." Gastroenterology 146(5):S17.
Extended European Search Report mailed on Jul. 21, 2015 issued in European Application No. 12854522.5, filed Oct. 8, 2014. 8 pages.
Extended European Search Report mailed on Nov. 16, 2017 issued in EP Application No. 15828951.2, filed on Aug. 10, 2015. 8 pages.
Extended European Search Report mailed on May 8, 2019 issued in European Application No. 18196397.6, filed Sep. 24, 2018. 12 pages.
Eissing, et al., (Feb. 1, 2012). "Pharmacogenomics of Codeine, Morphine, and Morphine-6-Glucuronide: Model-Based Analysis of the Influence of CYP2D6 Activity, UGT2B7 Activity, Renal Impairment, and CYP3A4 Inhibition." Molecular Diagnosis & Therapy 16(1):43-53.
Federal Register (Feb. 9, 2011). 76(27):7166. 14 pages.
Fukuda, et al. Jul. 2013). "Oral Session II-A (OII-A) Special Populations 3:45 pm-4:45 pm." Clinical Pharmacology & Therapeutics 93:S49-S51.
Fukuda, et al. (Feb. 2013). "Organic Cation Transport 1 genetic variants influence the pharmacokinetics of morphine in children." Pharmacogenomics 14(10):1141-1151.
Gasche, et al. (Dec. 30, 2004). "Codeine Intoxication Associated with Ultrarapid CYP2D6 Metabolism." The New England Journal of Medicine 351(27):2827-2831.
Gong, et al. (May 30, 2013). "Gene polymorphisms of OPRM1 A118G and ABCB1 C3435T may influence opioid requirements in Chinese patients with cancer pain." Asian Pacific Journal of Cancer Prevention 14(5):2937-2943.
Guyon, et al. (Jan. 2002). "Gene Selection for Cancer Classification using Support Vector Machines." Machine Learning 46:389-422.
Hacker, et al. (1997). "Lack of association between an interleukin-1 receptor antagonist gene polymorphism and ulcerative colitis." Gut 40:623-627.
Himes, et al. (Mar. 4, 2009). "Prediction of Chronic Obstructive Pulmonary Disease (COPD) in Asthma Patients Using Electronic Medical Records." Journal of the American Medical Informatics Association 16(3):371-379.
Hirschhorn, et al. (Mar. 2002). "A comprehensive review of genetic association studies." Genetics in Medicine 4(2):45-61.
Ioannidis, et al. (Oct. 15, 2001). "Replication Validity of Genetic Association Studies." Nature Genetics 15:306-309.
International Preliminary Report on Patentability mailed on Jun. 12, 2014 for International Application No. PCT/US2012/067111, filed Nov. 29, 2012. 7 pages.
International Preliminary Report on Patentability mailed on Sep. 9, 2016 for International Application No. PCT/US2015/017134, filed Feb. 15, 2015. 9 pages.
International Preliminary Report on Patentability mailed on Aug. 1, 2019 for International Application No. PCT/US2018/014405, filed Jan. 19, 2018. 10 pages.
International Search Report mailed on Mar. 20, 2013 issued for International Application No. PCT/US2012/067111, filed Nov. 29, 2012. 9 pages.
International Search Report mailed on Sep. 24, 2014 issued for International Application No. PCT/US2014/039357, filed May 23, 2014. 8 pages.
International Search Report mailed on Dec. 8, 2014 issued for International Application No. PCT/US2014/049301, filed Jul. 31, 2014. 8 pages.
International Search Report mailed on May 6, 2015 International Application No. PCT/US2015/017134, filed Feb. 23, 2015. 11 pages.
International Search Report and Written Opinion mailed on Oct. 24, 2019 received for PCT Patent International Application No. PCT/US2019/039411, filed Jun. 27, 2019. 10 pages.
Jannetto, et al. (May 18, 2011). "Pain management in the 21st century: utilization of pharmacogenomics and therapeutic drug monitoring." Expert Opinion on Drug Metabolism & Toxicology 7(6):745-752.
Juffali, et al. (2010). "The WiNAM project: Neural data analysis with applications to epilespy." Biomedical Circuits and Systems Conference 45-48.
Kelly, et al., (Apr. 9, 2012). "More codeine fatalities after tonsillectomy in North American children." Pediatrics 129(5):e1343-1347.
Kim, et al. (2006). "Genetic Predictors for Acute Experimental Cold and Heat Pain Sensitivity in Humans." Journal of Medical Genetics, e40 43(8):8 pages.
Kleine-Brueggeney, et al. (Dec. 15, 2010). "Pharmacogenetics in palliative care." Forensic Science international 203(1-3):63-70.
Larkin, et al. (2010). "A candidate gene study of obstructive sleep apnea in European Americans and African Americans." American Journal of Respiratory and Critical Care Medicine 182:947-953.
Laugsand, et al. (Apr. 11, 2011). "Clinical and genetic factors associated with nausea and vomiting in cancer patients receiving opioids." European Journal of Cancer 47(11):1682-1691.
Leschziner, et al. (Sep. 12, 2006). "ABCB1 genotype and PGP expression, function and therapeutic drug response: a critical review and recommendations for future research." The Pharmacogenomics Journal 7(3):154-179.
Lucentini, J. (Dec. 20, 2004). "Gene Association Studies Typically Wrong." The Scientist 18(24):20 . . . .
Meineke, et al. (Dec. 2002). "Pharmacokinetic modelling of morphine, morphine-3-glucuronide and morphine-6-glucuronide in plasma and cerebrospinal fluid of neurosurgical patients after short-term infusion of morphine." British Journal of Clinical Pharmacology 54(6):592-603.
Mizuno, et al. (2013). "Genotype of Abcc3-211c > T Influences the Pharmacokinetics of Morphine Glucuronide in Children." Clinical Pharmacology & Therapeutics 93:S63.
Mogil, et al. (Jul. 6, 1999). "The genetic mediation of individual differences in sensitivity to pain and its inhibition." Proceedings of the National Academy of Sciences 96(14):7744-7751.
Muller, et al. (Jan. 1, 2010). "Mutation Screen and Association Studies for the Fatty Acid Amide Hydrolase (Faah) Gene and Early Onset and Adult Obesity." BMC Medical Genetics 11:2.
Nies, et al. (2009). "Expression of organic cation transporters OCT1 (SLC22A 1) and OCT3 (SLC22A3) is affected by genetic factors and cholestasis in human liver." Hepatology 50(4):1227-1240.
Ozdas, et al. (Sep. 2004). "Investigation of Vocal Jitter and Glottal Flow Spectrum as Possible Cues for Depression and Near-Term Suicidal Risk." Transactions on Biomedical Engineering 51(9):1530-1540.
Park, et al. (Dec. 27, 2006). "Genetic polymorphisms in the ABCB1 gene and the effects of fentanyl in Koreans." Clinical Pharmacology & Therapeutics 81(4):539-546.
Pattinson, K. (May 1, 2008). "Opioids and the control of respiration." British Journal of Anaesthesia 100 (6):747-758.
Pennisi, E. (Sep. 18, 1998). "A Closer Look at SNPs Suggests Difficulties." Science 281(5384):1787-1789.
Partial European Search Report mailed on Feb. 2, 2019 issued in European Application No. 18196397.6, filed Nov. 29, 2012. 12 pages.
Prows, et al. (Nov. 13, 2013). "Codeine-related adverse drug reactions in children following tonsillectomy: a prospective study." Laryngoscope 124(5):1242-1250.

(56) References Cited

OTHER PUBLICATIONS

Ray, et al. (May 16, 2011). "Human Mu Opioid Receptor (OPRM1 A 118G) polymorphism is associated with brain mu-opioid receptor binding potential in smokers." Proceedings of the National Academy of Sciences 108(22):9268-9273.

Ross, et al. (Mar. 2008). "Genetic variation and response to morphine in cancer patients—Catechol-0-methyltransferase and multidrug resistance-1 gene polymorphisms are associated with central side effects." Cancer 112(6):1390-1403.

Sadhasivam, et al. (Apr. 1, 2010). "Pharmacogenetics and personalizing perioperative analgesia in children." Journal of Pain 11(4):01 page.

Sadhasivam, et al. (Apr. 23, 2012). "Race and unequal burden of perioperative pain and opioid related adverse effects in children." Pediatrics 129(5):832-838.

Sadhasivam, et al. (Jun. 13, 2012). "Preventing Opioid-Related Deaths in Children Undergoing Surgery." Pain Medicine 13(7):982-983.

Sadhasivam, et al. (Jul.-Aug. 2012). "Morphine clearance in children: does race or genetics matter?" Journal of Opioid Management 8(4):217-226.

Sadhasivam, et al. (2014). "Genetics of pain perception, COMT and postoperative pain management in children." The Pharmacogenomics Journal 15(3):277-284.

Sadhasivam, et al. (2015). "Novel Associations between FAAH Genetic Varients an Postoperative Central Opioid Related Adverse Effects." The Pharmacogenomics Journal 15(5):436-442.

Scherer, et al. (2013). "Investigating the Speech Characteristics of Suicidal Adolescents." International Conference on Acoustics, Speech and Signal Processing. 5 pages.

Shi, et al. (Sep. 15, 2010). "Biological pathways and genetic variables involved in pain." Quality of Life Research 119(10):1407-14717.

Shrestha, et al. (Feb. 10, 2016). "Epigenetic Regulations of GABAergic Neurotransmission: Relevance for Neurological Disorders and Epigenetic Therapy" Medical Epigenetics 4(1):1-19.

Shu, et al. (2007). "Effect of Genetic Variation in the Organic Cation Transporter 1 (OCT1) on Metformin Action." Journal of Clinical Investigation 117(5):1422-1431.

Sloan, et al.(May 10, 2012). "Genetic Variations and Patient-Reported Quality of Life Among Patients With Lung Cancer." Journal of Clinical Oncology 30(14):1699-1704.

SNPDEV (May 2, 2018). "Reference SNP (refSNP) Cluster Report: r5967935." Reference SNP (refSNP) Cluster Report: r5967935.

Stamer, et al. (Sep. 2008). "Respiratory Depression with Tramadol in a Patient with Renal Impairment and CYP2D6 Gene Duplication." International Anesthesia Research Society 107(3):926-929.

Stamer, et al. (Jun. 1, 2010). "Personalized therapy in pain management: where do we stand?" Pharmacogenomics 11(6):843-864.

Tzvetkov, et al. (Jul. 5, 2013) "Morphine is a substrate of the organic cation transporter OCT1 and polymorphisms in OCT1 gene affect morphine pharmacokinetics after codeine administration." Biochemical Pharmacology 86(5):666-678.

Venek, et al. (2014). "Adolescent Suicidal Risk Assessment in Clinician-Patient Interaction: A Study of Verbal and Acoustic Behaviors." Spoken Language Technology Workshop. 6 pages.

Venkatasubramanian, et al. (Jul. 2014). "ABCC3 and OCT1 genotypes influence pharmacokinetics of morphine in children." Pharmacogenomics 15(10):1297-1309.

Verspoor, et al. (Jun. 15, 2009). "The textual characteristics of traditional and Open Access scientific journals are similar." BMC Bioinformatics 10:183.

Wen, et al. (Aug. 23, 2013). "Molecular diagnosis of eosinophilic esophagitis by gene expression profiling." Gastroenterology 145(6):1289-1299.

Wen, et al. (Oct. 19, 2014). "Transcriptome analysis of proton pump inhibitor-responsive esophageal eosinophilia reveals proton pump inhibitor-reversible allergic inflammation." Journal of Allergy and Clinical Immunology 135(1):187-197.

Zheng, et al. (Jul. 26, 2006). "Extracting Principal Diagnosis, Co-Morbidity and Smoking Status for Asthma Research: Evaluation of a Natural Language Processing System." BMC Medical Informatics and Decision Making 6:30.

Zwisler, et al. (Aug. 2010). "The antinociceptive effect and adverse drug reactions of oxycodone in human experimental pain in relation to genetic variations in the OPRM1 and ABCB1 genes." Fundamental & Clinical Pharmacology 24(4):517-524.

International Search Report mailed on Nov. 9, 2015 for International Application No. PCT/US2015/044461, filed Aug. 10, 2015. 11 pages.

Adalsteinsson et al., "Heterogeneity in White Blood Cells Has Potential to Confound DNA Methylation Measurements," PLoS ONE, vol. 7, Issue 10: e46705 (9 pages) (Oct. 2012).

* cited by examiner

SEQUENCE LISTING

```
Sequence total quantity: 8
SEQ ID NO: 1              moltype = DNA  length = 25
FEATURE                   Location/Qualifiers
misc_feature              1..25
                          note = OPRM1_NF
source                    1..25
                          mol_type = other DNA
                          organism = synthetic construct
SEQUENCE: 1
taagaaatag taggagttgt ggtag                                           25

SEQ ID NO: 2              moltype = DNA  length = 22
FEATURE                   Location/Qualifiers
misc_feature              1..22
                          note = ORPM1_NR with biotinylation at 5' end
source                    1..22
                          mol_type = other DNA
                          organism = synthetic construct
SEQUENCE: 2
aaaaacacaa actatctctc cc                                              22

SEQ ID NO: 3              moltype = DNA  length = 27
FEATURE                   Location/Qualifiers
misc_feature              1..27
                          note = OPRM1_LF
source                    1..27
                          mol_type = other DNA
                          organism = synthetic construct
SEQUENCE: 3
tgtaagaaat agtaggagtt gtggtag                                         27

SEQ ID NO: 4              moltype = DNA  length = 25
FEATURE                   Location/Qualifiers
```

```
misc_feature            1..25
                        note = OPRM1_LR
source                  1..25
                        mol_type = other DNA
                        organism = synthetic construct
SEQUENCE: 4
aaataaaaca aattaaccca aaaac                                              25

SEQ ID NO: 5            moltype = DNA  length = 25
FEATURE                 Location/Qualifiers
misc_feature            1..25
                        note = OPRM1_S1/NF for CpG 1-7
source                  1..25
                        mol_type = other DNA
                        organism = synthetic construct
SEQUENCE: 5
taagaaatag taggagttgt ggtag                                              25

SEQ ID NO: 6            moltype = DNA  length = 24
FEATURE                 Location/Qualifiers
misc_feature            1..24
                        note = OPRM1_S2 for CpG 8-18
source                  1..24
                        mol_type = other DNA
                        organism = synthetic construct
SEQUENCE: 6
ggtgttttg gttatttggt atag                                                24

SEQ ID NO: 7            moltype = DNA  length = 27
FEATURE                 Location/Qualifiers
misc_feature            1..27
                        note = OPRM1_S3 for CpG 16 and 17
source                  1..27
                        mol_type = other DNA
                        organism = synthetic construct
SEQUENCE: 7
gtatttaagt tgtttttag tatttag                                             27

SEQ ID NO: 8            moltype = DNA  length = 26
FEATURE                 Location/Qualifiers
misc_feature            1..26
                        note = OPRM1_S4 for CpG site 18-22
source                  1..26
                        mol_type = other DNA
                        organism = synthetic construct
SEQUENCE: 8
gggttaattt gttttattta gatggt                                             26
```

METHODS AND COMPOSITIONS RELATING TO OPRM1 DNA METHYLATION FOR PERSONALIZED PAIN MANAGEMENT

RELATED APPLICATIONS

This application is a continuation of U.S. patent application Ser. No. 16/478,706, filed Jan. 19, 2018, which is a U.S. National Stage Application, filed under 35 U.S.C. § 371, of International Application No. PCT/US2018/014405, filed on Jan. 19, 2018, which claims the benefit of and priority under 35 U.S.C. § 119 to U.S. Provisional Application Ser. No. 62/448,540, filed Jan. 20, 2017, the entire content of which is incorporated herein by reference in its entirety.

This invention was made with government support under HD082782 awarded by the National Institutes of Health. The U.S. Government has certain rights in the invention.

TECHNICAL FIELD

The present invention relates to the field of medicine, and more particularly to the field of pain management, especially in the context of surgical pain.

SEQUENCE STATEMENT

The present application contains a Sequence listing in ASCII format. The ASCII copy, created on Feb. 28, 2023, is named 60250530C_ST26.xml and is 11,287 bytes in size, the content of which is hereby incorporated by reference in its entirety.

BACKGROUND

Inadequately controlled pain remains a significant problem after surgery, as it negatively affects quality of life, function, and increases risk of persistent postsurgical pain (Gan T J et al., 2014). Approximately 50-75% of patients undergoing surgery experience moderate or severe pain, and this is true for the six million children who undergo surgery every year in the United States (Polkki T et al., 2006; Kehlet H et al., 2006). Chronic postsurgical pain (CPSP) is the pain that lasts beyond two months postsurgery (Macrae W A, 2008). In children, the incidence of CPSP ranges from 13% to 68.8% (Landman Z et al., 2011; Page M G et al., 2013). This implies that of 1.5 million children who undergo major surgery every year in the US, about 225,000 to 1,000,000 children develop CPSP (Kain Z N et al., 1996). Inter-individual variability in pain sensitivity (LaCroix-Flalish M L et al., 2011), acute postsurgical pain (De Gregori M et al., 2016; Sadhasivam S et al., 2012; Sadhasivam S et al, 2014), and CPSP has been partly explained by genetic markers (Clake H et al., 2015) The mu-1 opioid receptor gene (OPRM1) that codes for the mu opioid receptor (MOR) plays an important role in opioid-pain pathways (Uhl G R et al., 1999). The OPRM1 variant that has been most commonly studied is the A118G variant; however, the results of association studies with pain and (β-endorphin-binding activity between this variant and the wild-type receptors is controversial (Branford R et al., 2012; Lee M G et al., 2016; Walter C et al., 2009; Beyer A et al., 2004).

Beyond genetics, chronic pain is a classic example of gene-environment interaction (Mogil J S, 2012), and hence recent interest has been directed toward the role of epigenetics in pain. Epigenetics is the study of changes in chromosomes that do not alter the sequence of deoxyribonucleic acid (DNA) (Bird A, 2007), but may still lead to alterations in gene expression. Genetics and epigenetics together are important factors in the transition of acute to chronic postsurgical pain (Buchheit T et al., 2012; Crow M et al., 2013). DNA methylation is a common epigenetic mechanism, which involves the addition of a methyl group to the 5' position of a cytosine residue followed by a guanine residue (a CpG dinucleotide), which are often clustered (CpG islands) in the promoter regions of genes (Ushijima T et al., 2006). DNA methylation at the OPRM1 promoter region regulates DNA binding of transcription factors and is a potent epigenetic repressor of gene transcription (Hwang C K et al., 2007).

Previous studies have shown that an increase in OPRM1 promoter methylation is associated with a decrease in protein expression of OPRM1 (Oertel B G et al., 2012). Because DNA methylation is reversible, there is much interest in understanding its association with pain, as a potential target for intervention. The OPRM1 DNA methylation levels have been found to be elevated in opioid and heroin addicts (Chorbov V M et al., 2011; Nielsen D A et al., 2009). However, this has not been studied in relation to perioperative pain and CPSP.

There is a need to identify clinical markers for predicting a patient's susceptibility to perioperative pain, opioid tolerance and hyperalgesia in order to provide improved management of pain in the clinical setting.

SUMMARY

The present invention is based, in part, on the discovery of OPRM1 methylation status as a biomarker of susceptibility to perioperative pain and opioid response, for example, opioid tolerance or hyperalgesia. Accordingly, the disclosure provides methods for pain management in the perioperative context, particularly through methods comprising assaying the DNA methylation status of the human OPRM1 gene at particular CpG sites in order to identify a patient as susceptible to perioperative pain. In embodiments, the methods may also be used to identify a patient as susceptible to an atypical opioid response, for example, opioid tolerance or hyperalgesia. The disclosure also provides related methods and compositions.

In embodiments, the disclosure provides a method for the prophylaxis or treatment of perioperative pain in a patient in need thereof, the method comprising assaying, in vitro, a biological sample from the patient to determine the DNA methylation status of at least one CpG site in the human mu-1 opioid receptor gene (OPRM1). In embodiments, the disclosure provides a method for identifying a patient who is susceptible to perioperative pain or an atypical opioid response, the method comprising assaying, in vitro, a biological sample from the patient to determine the DNA methylation status of at least one CpG site in the human mu-1 opioid receptor gene (OPRM1). In accordance with embodiments of the methods described here, the step of assaying a biological sample from the patient to determine the DNA methylation status of at least one CpG site in the OPRM1 gene includes detecting one or more 5-methylcytosine nucleotides in genomic DNA obtained from the sample. In embodiments, the step of assaying may further include one or more of isolating genomic DNA from the biological sample, treating the genomic DNA with bisulfate, and subjecting the genomic DNA to a polymerase chain reaction (DNA).

In embodiments, the perioperative pain is selected from preoperative pain, acute postoperative pain, and chronic postoperative pain. In embodiments, the perioperative pain is chronic postoperative pain.

In embodiments, the at least one CpG site in the OPRM1 gene is located between position −93 and position +159 of the human OPRM1 gene, relative to the transcription start site. In embodiments, the at least one CpG site is selected from the group consisting of sites 1-23 as defined in Table 4. In embodiments, the at least one CpG site is selected from CpG sites 1, 3, 4, 9, 11, and 17, preferably CpG site 11, as defined in Table 4, and the pain is preoperative pain. In embodiments, the at least one CpG site is selected from sites 4, 17, and 18, preferably CpG site 4, as defined in Table 4, and the pain is acute postoperative pain. In embodiments, the at least one CpG site is selected from sites 13 and 22, preferably CpG site 13, as defined in Table 4, and the pain is chronic postoperative pain.

In embodiments, the biological sample is a blood sample.

In embodiments, a patient having a DNA methylation status of 'methylated' at the at least one CpG site is identified as a patient susceptible to perioperative pain or an atypical response to opioids. In embodiments, a patient having a DNA methylation status of 'methylated' at the at least one CpG site is identified as a patient susceptible to opioid tolerance or hyperalgesia. In embodiments, the patient identified as susceptible is administered a therapeutic agent selected from a demethylating agent and an inhibitor of the repressor element-1 silencing transcription factor (REST). In embodiments the agent is administered before or after a surgical procedure is performed on the patient. In embodiments, the demethylating agent is selected from procaine, zebularine and decitabine, or a combination of two or more of the foregoing. In embodiments, the demethylating agent is zebularine, decitabine, or a combination of two or more of the foregoing.

In embodiments, the patient identified as susceptible is administered a regimen of multimodal analgesia for perioperative pain management. In embodiments, the regimen comprises administering to the patient one or more agents selected from the group consisting of acetaminophen, a nonsteroidal anti-inflammatory drug (NSAID), gabapentin, pregabalin, a TRPV1 agonist such as capsaicin, an NMDA receptor antagonist such as ketamine or memantine, an alpha-2 agonist such as clonidine and dexmedetomidine, a dual acting agent such as tapentadol, transdermal fentanyl, a long acting local anesthetic, a cannabinoid, or a combination of two or more of the foregoing. In embodiments, the administering of the one or more agents is before or after a surgical procedure is performed on the patient. In embodiments, the administering of at least one of the one or more agents is after a surgical procedure is performed on the patient In embodiments, the biological sample is assayed by a method comprising isolation of genomic DNA from the biological sample. In embodiments, the biological sample is assayed by a method comprising, or further comprising, pyrosequencing. In embodiments, the pyrosequencing comprises two or more rounds of a polymerase chain reaction.

In embodiments, the patient is a female patient.

In embodiments, the patient is self-reported Caucasian or white.

In embodiments, the disclosure provides a kit comprising a set of recombinant enzymes including one or more of DNA polymerase, ATP sulfurylase, luciferase, and apyrase, two substrates selected from one or both of adenosine 5' phosphosulfate (APS) and luciferin, at least one [biotinylated?] primer designed to amplify in a polymerase chain reaction a DNA segment corresponding to at least one of the CpG sites defined in Table 4, and a methylated DNA polynucleotide of known sequence, as a positive control

DETAILED DESCRIPTION

Figure 1:
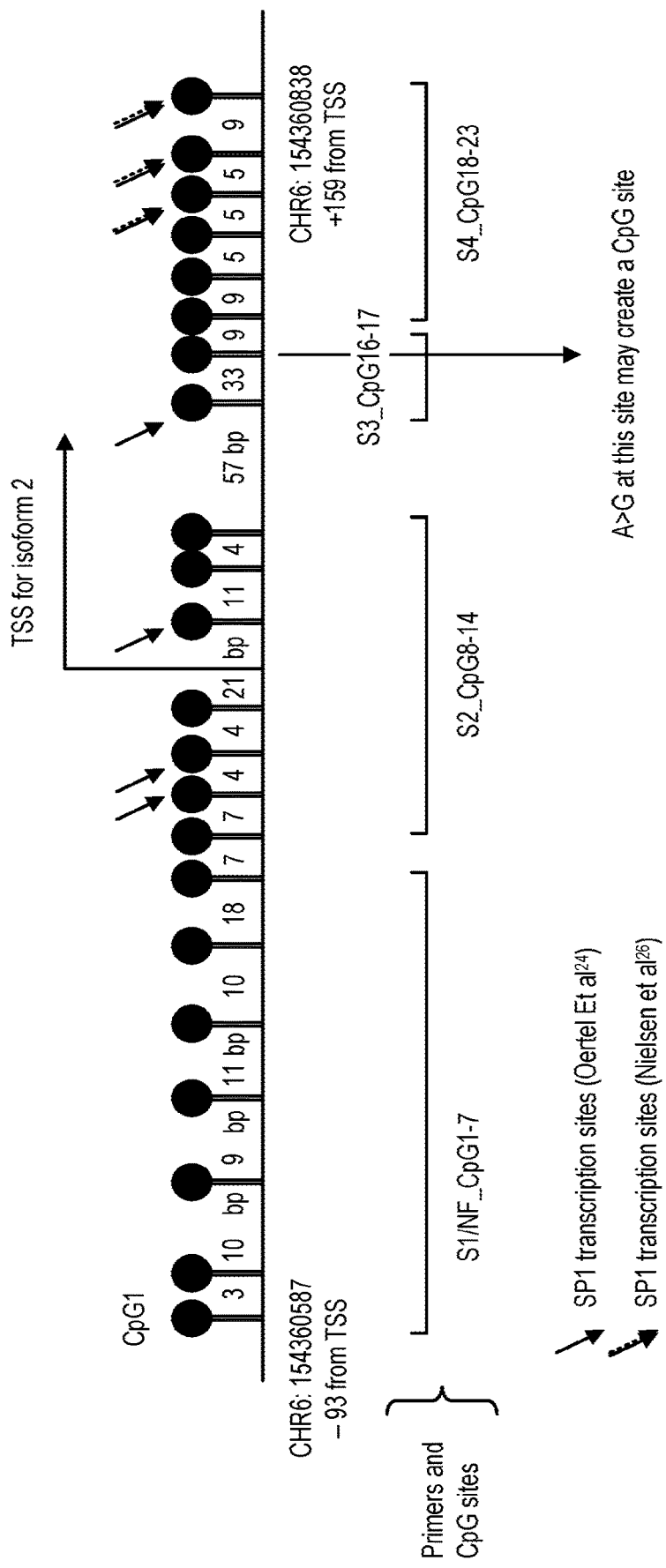
FIG. 1: Depiction of the OPRM1 promoter region (HG19; Chr 6: 154,360,587 to 154,360,838) and the location of the CpG sites. Knobs represent CpG sites; primers are indicated in brackets below. The light colored knob at +117 indicates the CpG site (CpG17) associated with the variant A118G. Arrows indicate sites that have been described as Sp1 transcription factor binding sites in previous studies, which are CpG sites 9, 10, 12, 16, 21, and 23 at −18, −14, +12, +84, +145, +150 and +159 from the ATG start site (transcriptional start site, or TSS).

The present disclosure is based, in part, on associations between epigenetic modifications in the genomic DNA of the OPRM1 gene, specifically methylation of certain CpG sites, especially in the promoter region of that gene, and preoperative pain, acute postoperative pain, and chronic postoperative pain following surgery. These findings allow for the identification of patients who are likely to be particularly susceptible to perioperative pain, especially acute and chronic postoperative pain. The ability to identify such patients allows for the development of targeted prevention and treatment regimens for acute and chronic postoperative pain. In addition, the patients identified by the methods described here may also be characterized as susceptible to an atypical opioid response, for example, opioid tolerance or hyperalgesia.

In the context of the present disclosure, the term "CpG site" refers to a site in genomic DNA where a cytosine nucleotide is followed by a guanine nucleotide when the linear sequence of bases is read in its 5 prime (5') to 3 prime (3') direction. The 'p' in "CpG" refers to a phosphate moiety and indicates that the cytosine and guanine are separated by only one phosphate group. A status of "methylated" in reference to a CpG site refers to methylation of the cytosine of the CpG dinucleotide to form a 5-methylcytosine.

In the context of the present disclosure, the terms "acute postoperative pain" and "chronic postoperative pain" are synonymous, respectively, with the terms "acute postsurgical pain" and "chronic postsurgical pain". The term "chronic postsurgical pain" may be abbreviated "CPSP". In this context, the term "chronic" refers to pain that persists for more than two months after surgery. Likewise, the term "acute" refers to pain occurring within the first two months after surgery.

In the context of the present disclosure, the term 'patient' refers to a human subject and a patient who is "susceptible" is one who is predisposed to suffering from perioperative pain, especially acute and chronic postsurgical pain. The identification of such patients according to the methods described here is intended to provide for more effective personalized pain management and, in embodiments, for the targeted prevention and/or treatment of acute and/or chronic postsurgical pain. For example, in embodiments, a patient is assayed for methylation status at the one or more CpG sites in OPRM1 as described herein before the patient is administered an opioid analgesic for the management of perioperative pain and the patient's CpG status is used to inform the patient's pain management protocol. In another embodiment, the patient may be assayed according to the methods described here after having received an opioid analgesic. In either case, the patient identified as susceptible to perioperative pain or as susceptible to having an atypical opioid response may be administered an agent to mitigate that susceptibility, such as a demethylating agent or an inhibitor of the repressor element-1 silencing transcription factor (REST). In embodiments, the demethylating agent may be selected from procaine, zebularine and decitabine, or a combination of two or more of the foregoing. In embodiments, the demethylating agent is zebularine, decitabine, or a combination of two or more of the foregoing. In embodiments, the patient identified according to the methods described here as susceptible to perioperative pain or as susceptible to having an atypical opioid response may be administered a regimen of multimodal analgesia for perioperative pain management. In embodiments, the regimen of multimodal analgesia may comprise administering to the patient one or more agents selected from the group consisting of acetaminophen, a nonsteroidal anti-inflammatory drug (NSAID), gabapentin, pregabalin, a TRPV1 agonist such as capsaicin, an NMDA receptor antagonist such as ketamine or memantine, an alpha-2 agonist such as clonidine and dexmedetomidine, a dual acting agent such as tapentadol, transdeimal fentanyl, a long acting local anesthetic, a cannabinoid, or a combination of two or more of the foregoing.

The term "opioid" is used to refer to medications acting through the opioid receptors and generally include substances such as morphine, fentanyl, hydromorphone, codeine, oxycodone, hydrocodone, tramadol, ondansetron, dexamethasone, methadone, alfentanil, remifentanil, and derivations thereof. Non-opioid medications include, for example, acetaminophen, NSAIDs, dexmedetomidine, clonidine, and combinations and derivations thereof.

In accordance with embodiments of the methods described here, the biological sample from the patient which is used to isolate genomic DNA and determine the methylation status of the OPRM1 gene is a blood sample. In these embodiments, blood is used as a proxy for the target tissue, brain, because brain tissue is generally inaccessible in the clinical context in which the present methods are performed. The use of blood as a substitute for various target tissues has been validated by others. For example, a comparison of methylation profiles of human chromosome 6, which is the chromosome on which the OPRM1 gene is located, derived from different twelve tissues showed that CpG island methylation profiles were highly correlated (Fan S et al., 2009). More recently, some inter-individual variation in DNA methylation was found to be conserved across brain and blood, indicating that peripheral tissues such as blood can have utility in studies of complex neurobiological phenotypes (Davies M N et al, 2012).

In accordance with embodiments of the methods described here, the methylation status at a genomic site, for example, at a CpG site as described herein, is binary, i.e., it is either methylated or unmethylated. In some embodiments where multiple CpG sites are assays, if at least one CpG site is methylated the region may be designated as methylated according to the claimed methods. This is because even if only one of several possible sites is methylated, if that site is a critical one for gene expression, its methylation may be sufficient. In other embodiments, where more than one of several possible CpG sites in a genomic region is methylated, the region may be designated as methylated or hypermethylated.

Methods of Assaying DNA Methylation Status

Embodiments of the methods described here include assaying a patient's genomic DNA to determine the DNA methylation status at one or more CpG sites in the human OPRM1 gene, particularly in a region of the OPRM1 gene defined by chromosomal positions 154,360,587 to 154,360,838 on chromosome 6 (with reference to the human genome build 38. In embodiments, the one or more CpG sites of the OPRM1 gene may also be defined as the CpG sites depicted in Table 4 at positions from −93 to +159 relative to the transcription start site, and designated as CpG sites 1-23 in Table 4.

As noted above, a status of "methylated" in reference to a CpG site refers to methylation of the cytosine of the CpG dinucleotide to form a 5-methylcytosine. Accordingly, methods of determining the DNA methylation status at one or more CpG sites in a genomic region of DNA generally involve detecting the presence of a 5-methylcytosine at the site, or multiple 5-methylcytosine in the region of interest. The determination of DNA methylation status can be performed by methods known to the skilled person. Typically such methods involve a determination of whether one or more particular sites are methylated or unmethylated, or a determination of whether a particular region of the genome is methylated, unmethylated, or hypermethylated, through direct or indirect detection of 5-methylcytosine at a particular CpG site, or in the genomic region of interest.

Whole genome methylation can be detected by methods including whole genome bisulfite sequencing (WEBS), high performance liquid chromatography liquid chromatography (HPLC) coupled with tandem mass spectrometry (LC-MS/MS), enzyme-linked immunosorbent assay (ELISA)-based methods, as well as amplification fragment length polymorphism (AFLP), restriction fragment length polymorphism (FRLP) and luminometric methylation assay (LUMA).

Generally, in the context of the methods described here, the methylation status of one or more specific CpG sites is determined. Suitable methods may include bead array, DNA amplification utilizing a polymerase chain reaction (PCR) followed by sequencing, pyrosequencing, methylation-specific PCR, PCR with high resolution melting, cold-PCR for the detection of unmethylated islands, and digestion-based assays. Bisulfite conversion is typically an initial step in these methods. Accordingly, in embodiments, the method for assaying DNA methylation status in accordance with the present disclosure may include a step of bisulfite conversion, for example a step of treating a sample of genomic DNA with bisulfite thereby converting cytosine nucleotides to uracil nucleotides except where the cytosine is methylated.

In embodiments, the step of assaying DNA methylation status comprises pyrosequencing. The analysis of DNA methylation by pyrosequencing is known in the art and can be performed in accordance with published protocols, such as described in Delaney et al, *Methods Mol Biol.* 2015 1343:249-264. This technique detects single-nucleotide polymorphisms which are artificially created at CpG sites through bisulfite modification of genomic DNA, which selectively converts cytosine to uracil except where the cytosine is methylated, in which case the 5-methylcytosine is protected from deamination and the CG sequence is preserved in downstream reactions. Generally, the method comprises treating extracted genomic DNA with bisulfite and amplifying the DNA segment of interest with suitable primers, i.e., using a PCR based amplification. In accordance with the methods of the present disclosure, suitable primers for use in the methods described here may be based on those shown in Table 2, which are designed for detecting the methylation status at the specific CpG sites in the OPRM1 gene described herein.

Demethylating Agents

DNA demethylating agents inhibit DNA methyltransferases (DNMTs) such as DNMT1, which is responsible for the maintenance of methylation patterns after DNA replication, DNMT3A, and DNMT3B, each of which carries out de novo methylation.

In accordance with certain embodiments of the methods described here, a patient identified as susceptible to perioperative pain based on the patient's OPMR1 methylation status as described herein, including a patient identified as susceptible to opioid tolerance or hyperalgesia, may be administered one or a combination of two or more demethylating agents, for example, as part of a personalized pain management regimen.

In embodiments, a demethylating agent administered in accordance with embodiments of the methods described here may be a nucleoside-like DNMT inhibitor or a nonnucleoside DNMT inhibitor.

In an embodiment, the agent is a nucleoside-like DNMT inhibitor. In embodiments, the nucleoside-like DNMT inhibitor is selected from azacytidine (VIDAZA™), and analogs thereof, including 5-aza-2'-deoxycytidine (decitabine, 5-AZA-CdR), 5-fluoro-2'-deoxycytidine, and 5,6-dihydro-5-azacytidine. In embodiments, the nucleoside-like DNMT inhibitor is selected from yrimidine-2-one ribonucleoside (zebularine).

In an embodiment, the agent is a nonnucleoside-like DNMT inhibitor. In embodiments, the agent is an antisense oligonucleotide. In embodiments, the antisense oligonucleotide is MG98, a 20-base pair antisense oligonucleotide that binds to the 3' untranslated region of DMNT1, preventing transcription of the DNMT1 gene. In embodiments, the nonnucleoside-like DNMT inhibitor is RG108, a small molecule DNA methylation inhibitor (Graca I et al., *Curr Pharmacol Design.* 2014 20:1803-11).

REST Inhibitors

In accordance with embodiments of the methods described here, a patient identified as susceptible to perioperative pain based on the patient's OPMR1 methylation status as described herein, including a patient identified as susceptible to opioid tolerance or hyperalgesia, may be administered an inhibitor of the repressor elements-1 silencing transcription factor (REST). In embodiments, the REST inhibitor is denzoimidazole-5-carboxamide derivative (X5050) (Charbord J et al., 2013).

Multimodal Analgesia

In accordance with embodiments of the methods described here, a patient identified as susceptible to perioperative pain based on the patient's OPMR1 methylation status as described herein, including a patient identified as susceptible to opioid tolerance or hyperalgesia, may be administered a regimen of multimodal analgesia. The aim of such a regimen is to employ agents with different mechanisms of analgesia that may have synergistic effects on pain management when administered in combination. See e.g., the discussion by Asokumar Buvanendran in *Int'l Anesthesia Res.* (2011). Preferably, the regimen is tailed to the individual patient. Examples of agents and classes of agents that may form part of a regimen of multimodal analgesia include acetaminophen, a nonsteroidal anit-inflammatory drug (NSAID), gabapentin, pregabalin, a TRPV1 agonist such as capsaicin, an NMDA receptor antagonist such as ketamine or memantine, an alpha-2 agonist such as clonidine and dexmedetomidine, a dual acting agent such as tapentadol, transdeimal fentanyl, a long acting local anesthetic, a cannabinoid, and combinations of any two or more of the foregoing. In embodiments, one or more of the foregoing agents is used as an adjunct to treat pain in the perioperative patient.

Target Population

In embodiments of the methods described here, the methods are directed to a target population of patients in need of prophylaxis or treatment of peri operative pain. In embodiments, the target patient population may be further defined as discussed below. In the context of the methods described here, the term "patient" refers to a human subject. In embodiments, the term may more particularly refer to a human subject under the care of a medical professional.

In embodiments, the target patient population may be further defined by sex, age, or self-reported human population or ethnic group. For example, in embodiments the patient is a female. In embodiments, the patient is an adolescent, as that term is understood by the skilled medical practitioner. In embodiments, the patient's race or ethnicity is self-reported as white or Caucasian.

Kits

Kits useful in the methods disclosed here comprise components such as primers for nucleic acid amplification, hybridization probes, means for analyzing the methylation state of a deoxyribonucleic acid sequence, and the like. The kits can, for example, include necessary buffers, nucleic acid primers, and reagents for detection of methylation, as well as suitable controls, including for example bisulfite conversion controls, such as a bisulfite treated DNA oligonucleotide of known sequence, and template free negative controls for pyrosequencing, as well as necessary enzymes (e.g. DNA polymerase), and suitable buffers.

In some embodiments, the kit comprises one or more nucleic acids, including for example PCT primers and bisulfite treated DNA for use as a control, for use in the detection of the methylation status of one or more of the specific CpG sites identified herein, as well as suitable reagents, e.g., for bisulfite conversion, for amplification by PCR and/or for detection and/or sequencing of the amplified products.

In embodiments, the kit comprises a set of PCR primers for detecting the methylation status of one or more of the CpG sites identified herein. In embodiments, the kit comprises at least two sets of primers, long and nested.

In embodiments, the kit comprises a set of PCR primers including two or more primers identified by SEQ ID NOs 1-8 herein.

In certain embodiments, the kit further comprises a set of instructions for using the reagents comprising the kit.

Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, NY 2001); March, *Advanced Organic Chemistry Reactions, Mechanisms and Structure* 5$^{th}$ ed., J. Wiley & Sons (New York, NY 2001); and Sambrook and Russel, *Molecular Cloning: A Laboratory Manual* 3$^{rd}$ ed., Cold Spring Harbor Laboratory Press (Cold Spring Harbor, NY 2001) provide one skilled in the art with a general guide to many of the terms used in the present application.

All percentages and ratios used herein, unless otherwise indicated, are by weight. Other features and advantages of the present disclosure are apparent from the different examples set forth below. The examples illustrate different components and methodology useful in practicing aspects of the present disclosure. The examples do not limit the claimed disclosure. Based on the present disclosure the skilled artisan can identify and employ other components and methodology useful for practicing the methods described here.

Examples

Methods

A prospective observational cohort study was conducted in 133 adolescents with idiopathic scoliosis undergoing posterior spine fusion under standard intraoperative anesthesia (propofol-remifentanil total intravenous anesthesia, guided by electroencenphalography monitoring for depth of anesthesia) and postoperative analgesia with morphine patient-controlled analgesia (PCA) with adjuvant (scheduled intravenous acetaminophen, ketorolac, and diazepam as needed and methocarbamol) managed by perioperative pain team. The study was approved by the Cincinnati Children's Hospital Medical Center (CCHMC) institutional review board. This study was registered with Clinicaltrials.gov identifiers NCT01839461 and NCT01731873. Written informed consent was obtained from parents, and assent was obtained from children before enrollment.

Participants

Healthy non-obese subjects with an American Society of Anesthesiologists (ASA) physical status less than or equal to two (mild systemic disease), aged ten to eighteen years, with a diagnosis of idiopathic scoliosis and/or kyphosis, undergoing elective spinal fusion were recruited. The exclusion criteria included pregnant or breastfeeding females, presence of chronic pain defined as use of opioids in the past six months, liver or renal diseases, and developmental delays.

Data Collection

Preoperatively, data regarding demographic factors (sex, age, and race), weight, pain scores (numerical rating scale (NRS)/0-10) (von Bayer C L, 2009) on the day of surgery (P0), and pain medications used were obtained. Anxiety scores for both child and a parent were assessed using the 0-10 visual analog scale (VAS), a simple validated scale which has been used previously in children (Bringuier S et al., 2009) Questionnaires were administered as described in the following sections. The intraoperative data collected included propofol and remifentanil doses, duration of surgery, and number of vertebral levels fused. In the immediate postoperative period (postoperative days (PODs) one and two), pain scores (every four hours), morphine and diazepam doses administered were noted. After hospital discharge, the questionnaires were administered per the schedule presented in Table 1 to obtain psychosocial and pain measures in a standard fashion.

TABLE 1

Data collection scheme

| Data variants | Preoperative | Intraoperative | 2-3 months |
|---|---|---|---|
| Demographics | X | | |
| Anxiety score | | | |
| Surgical duration | | X | |
| Vertebral levels fused | | | |
| Propofol dose | | | |
| Remifentanil dose | | | |
| Pain scores | X | | X |
| Opioid consumption | | | |
| Diazepam use | | | |
| Analgesic adjucts | | | |
| Qustionnnaires | | | |
| CASI | X | | X |
| PCS-C | | | |
| FDI | | | |
| Pain assessment | | | |
| Questionnaires | | | |
| PPH | X | | |
| PCS-P | | | |

Notes:
Time calculated from end of surgery. X indicates the phase in which the data is collected.
Abbreviations: CASI, Child Anxiety Sensitivity Index; PCS-C, pain catastrophizing scale (child version); FDI, functional disability index; PPH, parent pain history; PCS-P, pain catastrophizing scale (parent version).

Outcomes

Pain outcomes evaluated were a) preoperative pain, b) acute postoperative pain (defined as Area under Curve (AUC) for pain scores over time on postoperative day one and two ($AUC_{POD1-2}$) calculated using trapezoidal rule) and c) chronic pain/CPSP (NRS>3/10 at two to three months postsurgery) as defined by the International Association for the Study of Pain (Macrae WA, 2009). These cut-offs for NRS were used because NRS pain scores >3 (moderate/severe pain) at three months has been described as a predictor for persistence of pain and associated with functional disability (Gerbershagen H K et al., 2011)

Measurement of DNA Methylation

Blood was drawn upon intravenous line placement before surgery, from which DNA was isolated on the same day and frozen at −20° C. To study DNA methylation, we focused on a 251 base pair (bp) region, including 22 CpG sites reaching from position −93 to position +159, whose methylation levels were previously shown to associated with the OPRM1 expression (Oertel B G et al., 2012) and opioid/heroin addiction (Chorbov V M et al., 2011; Nielsen D A et al., 2009) (FIG. 1). The CpG sites are numbered according to those studies for ease of comparison. This included a CpG site at +117, reported by Oertel et al (Oertel B G et al., 2012). The pyrosequencing assays utilize 50-500 ng of genomic DNA of acceptable quality measured by NanoDrop spectrophotometer (Thermo Scientific, Waltham, MA, USA) and with a 260/280 ratio ranging from 1.6 to 2.0). The extracted DNA was treated with bisulfite using Zymo EZ DNA Methylation Gold kit (Zymo Research, Orange, CA, USA), according to the manufacturer's instructions. Two sets of primers, long and nested, were designed using Zymo Taq Premix for two rounds of polymerase chain reaction (PCR). Methylation of the PCR products was quantified using PyroMark MD 1.0 software (Qiagen, Valencia, CA, USA). Primers used in the assays are listed in Table 2. Samples were repeated if the pyrosequencing runs do not pass quality checks of the pyrosequencer or if the internal bisulfate conversion controls failed. The sample runs were monitored through methylated and nonmethylated DNA as well as template-free negative controls.

CPSP using logistic regression models. Covariables associated at $P<0.10$ were entered into multivariable models and stepwise selection was used to derive a final non-genetic model for each outcome where only variables with $P<0.05$ were retained (Bursac Z et al., 2008). DNA methylation levels were then added to the final nongenetic model to assess its association with the pain outcomes. Statistical analyses were performed using Statistical Analysis System (SAS), version 9.3 (SAS Institute Inc., Cary, NC, USA). $P \leq 0.05$ was used as the threshold for statistical significance. No multiple testing correction was done, thus it is possible that some findings occurred by chance.

Functional Genomics Analysis

To identify potential regulatory mechanisms in the OPRM1 promoter, a large collection of functional genomics datasets from various sources, including encyclopedia of

TABLE 2

Primers used in the Pyrosequencing assay

| Primer | Forward | CpG sites | SEQ ID NO |
|---|---|---|---|
| OPRM1_NF | 5'-TAAGAAATAGTAGGAGTTGTGGTAG-3' | | 1 |
| OPRM1_NR | 5'-Biotin-AAAAACACAAACTATCTCTCCC-3' | | 2 |
| OPRM1_LF | 5'-TGTAAGAAATAGTAGGAGTTOTGGTAG-3' | | 3 |
| OPRM1_LR | 5'-AAATAAAACAAATTAACCCAAAAAC-3' | | 4 |
| OPRM1_S1/NF | 5'-TAAGAAATAGTAGGAGTTGTGGTAG-3' | CpG1-7 | 5 |
| OPRM1_S2 | 5'-GGTGTTTTTGGTTATTTGGTATAG-3' | CpG8-14 | 6 |
| OPRM1_S3 | 5'-GTATTTAAGTTGTTTTTAGTATTTAG-3 | CpG 16 and 17 (SNP-CpG) | 7 |
| OPRM1_S4 | 5'-GGGTTAATTTGTTTTATTTAGATGGT-3' | CpG18-22 | 8 |

NF and NR are the forward and reverse primers used in the $2^{nd}$ round, nested PCR; LF and LR are the forward and reverse primers used in the $1^{st}$ round, long PCR.

Data Analysis

Prior to the analyses, the data quality was assessed. Demographics and patients' clinical characteristics were summarized as mean (standard deviation, SD), median (interquartile range, IQR) and frequency (percentage) according to the distribution of the data. Prior to evaluation of the association between pain outcome and DNA methylation, the effects of covariables were tested (paper), which included age, sex, race, morphine dose in mg/kg on POD1 and 2, preoperative anxiety score (VAS), preoperative pain score, duration of surgery, vertebral levels fused, propofol and remifentanil doses used during surgery (per kg), use of intravenous acetaminophen/ketorolac (yes/no), diazepam doses (mg/kg), and pain catastrophizing scale parent version (PCS-P), parent pain history (PPH) scores and sequential scores for Childhood Anxiety Sensitivity Index (CAST) and pain catastrophizing scale child version (PCS-C). Three pain outcomes were examined. Preoperative pain was dichotomized as yes versus no, because, although it was measured using NRS as a 0-10 scale, 83% of the patients reported no preoperative pain. It was then associated with covariables using logistic regression. Similarly, acute postoperative pain was analyzed using simple linear regression models, and DNA elements (ENCODE) (Consortium EP, 2012), Roadmap Epigenomics (Bernstein B E et al., 2010), Cistrome (Li T et al., 2011), and ReMap-ChIP (Griffon A et al., 2015), was compiled. The genomic coordinates of the OPRM1 promoter were intersected against the genomic coordinates contained in each dataset. In total, this database contains 4,953 datasets performed in 1,706 different cell types and conditions; 1,911 datasets monitor binding interactions of transcription factors with the human genome using ChIP-seq; 1,214 measure the presence of a particular histone mark using ChIP-seq; 226 measure open chromatin through DNase-seq; 57 measure expression quantitative loci (eQTLs); and 558 predict "ActiveChromatin" states using combinations of histone marks (Ernst J et al., 2011). Collectively, 240 of these experiments were performed in brain-related cell lines and cell types.

Results

Figure 2:
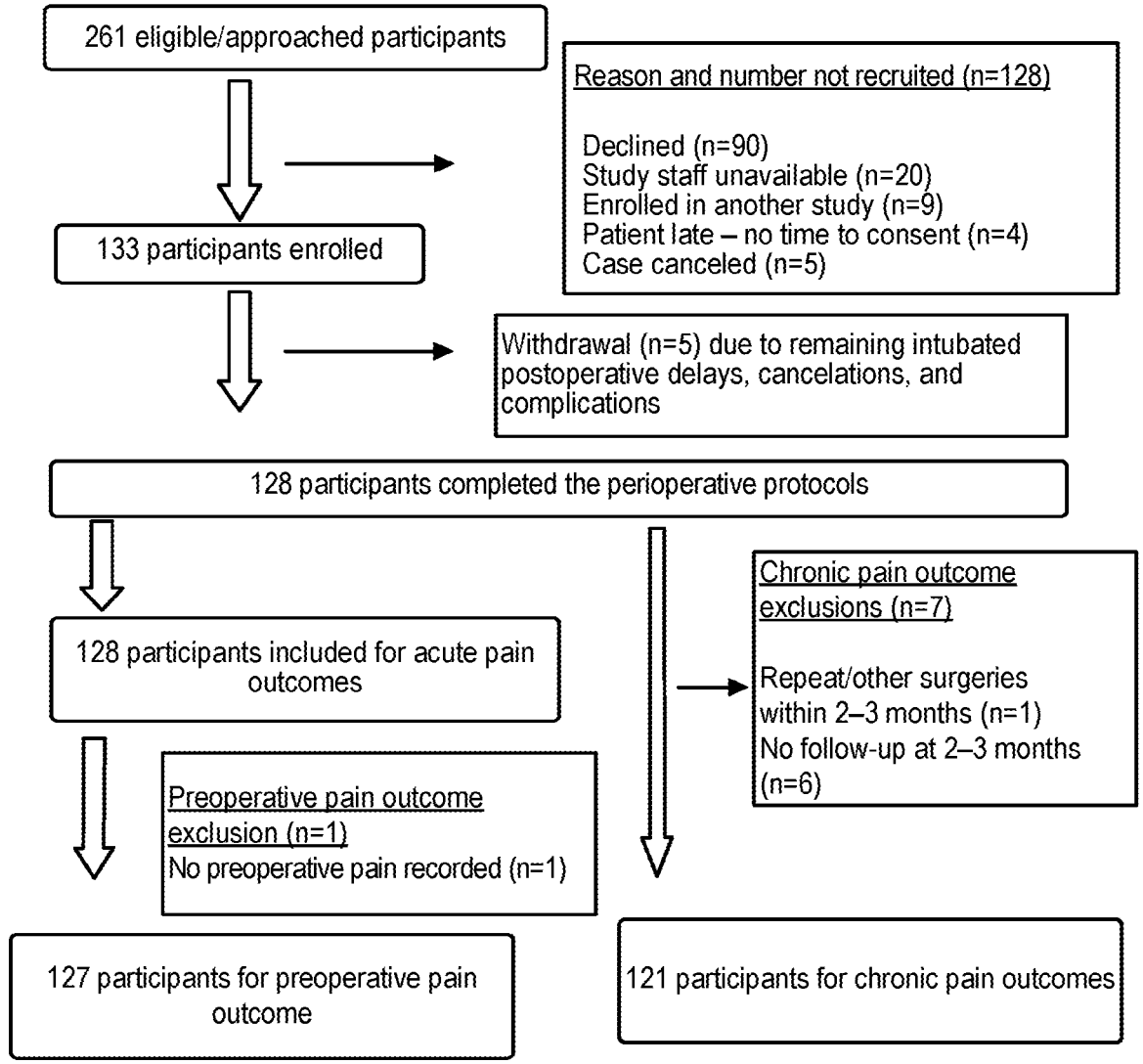
FIG. 2: Recruitment timeline for the spine surgery study cohort. Of 261 eligible patients who satisfied inclusion/exclusion criteria, reasons for not enrolling and derivation of final cohorts included in the study with preoperative, acute and chronic pain outcomes are described.

The final cohort was composed of 133 participants; the mean age was 14.49 years (SD 1.91) and they were mostly white (83%) and female (74%) (Table 3). The recruitment timeline is described in FIG. 2. Descriptions of variables that were evaluated for inclusion in the multiple regression model are presented in Table 3.

TABLE 3

Demographic of the cohorts and description of covariants used in the regression model

|  | Acute (N = 128) | [d]p-value | Chronic Pain (CP) | | |
|---|---|---|---|---|---|
|  |  |  | No (N = 77) | Yes (N = 44) | p-value |
| [a]Age (years) | 14.49 ± 1.91 | 0.15 | 14.20 ± 1.87 | 14.78 ± 1.67 | 0.1 |
| [b]Sex |  | 0.23 |  |  | 0.54 |
| Male | 35 (26%) |  | 20 (26%) | 9 (21%) |  |
| [b]Race |  | 0.21 |  |  | 0.13 |
| White | 111 (83%) |  | 66 (86%) | 32 (74%) |  |
| [c]Weight (Kg) | 54.00 (48.00-61.90) | 0.83 | 54.20 (48.00-61.9) | 54.00 (50.00-61.00) | 0.9 |
| [c]VAS Anxiety (Child) | 4.30 (2.50-6.80) | 0.24 | 4.40 (2.60-6.80) | 3.60 (1.80-5.20) | 0.39 |
| [c]VAS Anxiety (Parent) | 5.50 (4.36-8.00) | 0.24 | 5.40 (4.60-8.00) | 5.90 (4.40-8.10) | 0.94 |
| [c]Preoperative pain score | 0.00 (0.00-0.00) | <0.001 | 0.00 (0.00-0.00) | 0.00 (0.00-2.00) | 0.015 |
| [c]Number of vertebral levels fused | 12.00 (11.00-12.00) | 0.58 | 12.00 (11.00-12.00) | 12.00 (10.00-12.00) | 0.91 |
| [a]Surgical duration (hours) | 4.91 ± 1.27 | 0.21 | 4.71 ± 1.07 | 5.09 ± 1.45 | 0.14 |
| [a]PainAUC POD1&2 | 198.58 ± 73.78 |  | 189.04 ± 67.61 | 222.64 ± 80.44 | 0.018 |
| [c]Morphine dose POD1&2 (mg/kg) | 1.60 (1.19-2.17) | 0.15 | 1.59 (1.08-1.93) | 1.89 (1.50-2.47) | 0.003 |
| [a]CASI | 28.21 ± 5.87 | 0.18 | 27.86 ± 5.99 | 28.38 ± 5.80 | 0.71 |

Note:
[a]data exhibited normal distribution; shown as mean ± SD and compared using t tests for CP.
[b]frequency (proportion) and compared using Chi-squared tests for CP.
[c]data did not exhibit a normal distribution; shown as median (IQR) and compared using Wilcoxon rank sum tests for CP.
[d]assessed using Spearman's rank correlation

Pain Descriptives

Acute and chronic postoperative pain data were collected for 128 and 121 patients, respectively. The overall incidence of CPSP was found to be 36.4% (44/121). The preoperative pain score was 0 in 83% (106/127) of the cohort.

DNA Methylation and Pain

Figure 3:
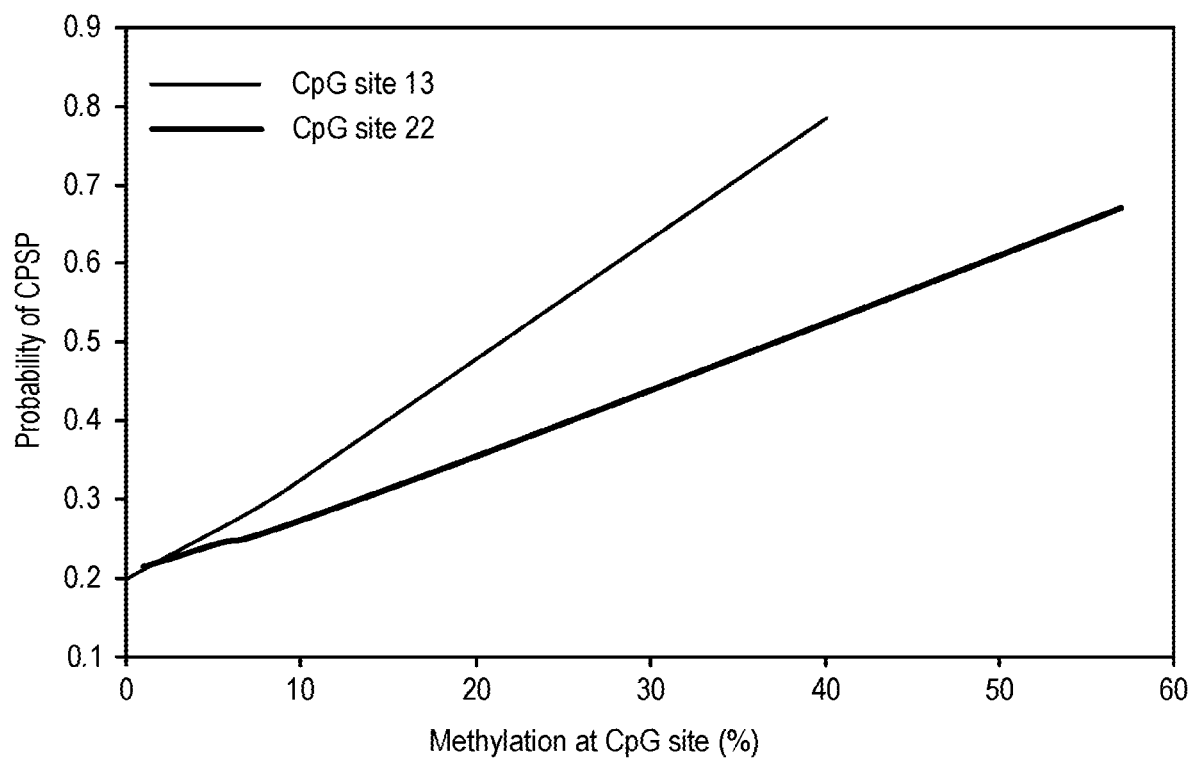
FIG. 3: Probability of developing CPSP based on DNA methylation at CpG 13 and 22, derived from the regression model, is depicted. The probabilities were estimated using median preoperative pain scores (0), median morphine consumption (1.7 mg/kg), and 2.5%, 25%, 50% 75%, and 97.5% of the methylation data of each of the two sites. The 97.5% values for DNA methylation in the data are 40% for CpG13 and 57% for CpG22. The nongenetic covariates are already adjusted for in the regression model. Hence, the probability of CPSP holding other variables constant increases with increased methylation at these sites.

Three pain outcomes were examined. For the association with dichotomized preoperative pain scores, logistic regression was used. After adjusting for age and sex, the methylation level of six CpG sites (sites 1, 3, 4, 9, 11 and 17, Table 4) was significantly associated with whether a patient reported preoperative pain. For all the six CpG sites, higher methylation was associated with higher odds of reporting preoperative pain, except for site 17. No impact of the methylation on the actual pain scores was detected (data not shown). For acute postoperative pain ($AUC_{POD1-2}$), significant impact of methylation was detected in CpG sites 4, 17 and 18 (Table 4) when preoperative pain and morphine consumption were adjusted. For all three CpG sites, higher methylation was associated with higher preoperative pain. For chronic postoperative pain, significant association was detected for the nonpromoter site, CpG13 and 22 (Table 4), with preoperative pain and morphine consumption being controlled. For all the CpG sites, higher methylation was associated with higher odds of having chronic pain. Methylation at two CpG sites was associated with both preoperative pain and $AUC_{POD1-2}$ (CpG4 and 17); methylation at these sites also showed a trend toward CPSP risk, although not statistically significant. FIG. 3 depicts estimated probabilities of developing CPSP using median preoperative pain score (0), median morphine doses (1.7 mg/kg), and 2.5%, 25%, 50%, 75% and 97.5% of the methylation data of each of the two sites CpG13 and CpG22.

TABLE 4

Association of DNA methylation of CpG sites at the OPRM1 promoter with pain outcomes

| | Location from ATG | | [a]Preop pain score of 1 | | [b]Acute pain | | [c]CPSP | | |
|---|---|---|---|---|---|---|---|---|---|
| CpG site | site Chr6 154,360,680 | Genomic location | P value | Regression coefficient | P value | Regression coefficient | P value | Regression coefficient | OR (95% CI) |
| 1 | -93 | 154360587 | 0.023 | 0.051 | 0.29 | 0.62 | 0.189 | -0.028 | 0.972 (0.932-1.015) |
| 2 | -90 | 154360590 | 0.256 | 0.023 | 0.464 | 0.396 | 0.452 | 0.014 | 1.014 (0.978-1.053) |
| 3 | -80 | 154360600 | 0.035 | 0.041 | 0.153 | 0.772 | 0.368 | -0.017 | 0.983 (0.946-1.021) |
| 4 | -71 | 154360609 | 0.026 | 0.054 | 0.003 | 1.864 | 0.995 | 0 | 1.000 (0.957-1.046) |
| 5 | -60 | 154360620 | 0.916 | -0.003 | 0.495 | 0.412 | 0.411 | 0.017 | 1.017 (0.977-1.060) |
| 6 | -50 | 154360630 | 0.589 | 0.009 | 0.1 | 0.836 | 0.731 | 0.006 | 1.006 (0.973-1.040) |
| 7 | -32 | 154360648 | 0.145 | 0.019 | 0.221 | 0.466 | 0.567 | 0.007 | 1.007 (0.983-1.033) |
| 8 | -25 | 154360655 | 0.198 | 0.021 | 0.875 | -0.07 | 0.227 | 0.019 | 1.019 (0.988-1.050) |
| 9 | -18 | 154360662 | 0.02 | 0.038 | 0.925 | 0.044 | 0.548 | 0.01 | 1.010 (0.978-1.043) |
| 10 | -14 | 154360666 | 0.979 | 0.001 | 0.886 | -0.097 | 0.893 | 0.003 | 1.003 (0.958-1.051) |
| 11 | -10 | 154360670 | 0.008 | 0.049 | 0.443 | 0.404 | 0.147 | 0.029 | 1.029 (0.989-1.071) |
| 12 | 12 | 154360691 | 0.716 | 0.013 | 0.5 | 0.625 | 0.117 | 0.051 | 1.052 (0.985-1.124) |
| 13 | 23 | 154360702 | 0.305 | 0.018 | 0.46 | 0.356 | 0.002 | 0.067 | 1.069 (1.022-1.119) |
| 14 | 27 | 154360706 | 0.81 | -0.006 | 0.444 | 0.441 | 0.793 | 0.006 | 1.006 (0.964-1.049) |
| 16 | 84 | 154360763 | 0.221 | 0.069 | 0.73 | 0.512 | 0.15 | 0.073 | 1.075 (0.973-1.188) |

TABLE 4-continued

Association of DNA methylation of CpG sites at the OPRM1 promoter with pain outcomes

| CpG site | Location from ATG | Genomic location | $^{a Preop}$pain score of 1 | | $^{b Acute}$pain | | $^{c CPSP}$ | | |
|---|---|---|---|---|---|---|---|---|---|
| | site Chr6 154,360,680 | | P value | Regression coefficient | P value | Regression coefficient | P value | Regression coefficient | OR (95% CI) |
| 17 | 117 | 154360796 | 0.029 | −0.997 | 0.034 | 17.736 | 0.114 | 0.516 | 1.675 (0.885-3.171) |
| 18 | 126 | 154360805 | 0.205 | 0.019 | 0.031 | 0.921 | 0.804 | 0.004 | 1.004 (0.975-1.033) |
| 19 | 135 | 154360814 | 0.334 | 0.019 | 0.415 | 0.418 | 0.856 | −0.003 | 0.997 (0.962-1.033) |
| 20 | 140 | 154360819 | 0.151 | 0.025 | 0.826 | 0.108 | 0.977 | −0.001 | 1.000 (0.966-1.034) |
| 21 | 145 | 154360824 | 0.103 | 0.029 | 0.914 | 0.053 | 0.861 | 0.003 | 1.003 (0.970-1.038) |
| 22 | 150 | 154360829 | 0.446 | 0.014 | 0.314 | 0.497 | 0.046 | 0.036 | 1.037 (1.000-1.075) |
| 23 | 159 | 154360838 | 0.491 | 0.023 | 0.385 | 0.75 | 0.48 | 0.022 | 1.022 (0.964-1.083) |

Functional Genomics Analysis

Query of the region evaluated using a large collection of ChIP-seq, DNase-seq and eQTL data as described in the "Methods" section, showed that this region is located in open chromatin and is marked by H3K27ac, H3K4mel, and H3K4me3 (indicative of active regulatory regions) (Koch C M et al., 2007; Barski A et al., 2007; Creyghton M P et al., 2010) in non-cancer brain cells from the caudate-putamen, temporal, frontal lobes and angular gyri. Moreover, this region contains ChIP-seq peaks for binding of multiple transcription factors, including RE1 silencing transcription factor (REST), RAD21, Specificity protein 1 (SP1), Yin and Yang 1 (YY1), and zinc finger protein 263 (ZNF263) in various tissues. In particular, REST and RAD21 binds the OPRM1 promoter region in three cell lines (SK-N-SH, PFSK-1 and SK-N-SH cell lines) derived from brain tissue where the opioid receptors responsible for analgesia are found (Table 5). Collectively, these results suggest that the differential DNA methylation patterns observed in the OPRM1 promoter might functionally act by modulating the expression of OPRM1 via alteration of the binding of REST and other neuron-expressed transcription factors.

TABLE 5

Findings from evaluation of OPRM1 promoter region using functional genomics datasets in neuronal cell-type

| Data set name | Type | Cell-type label |
|---|---|---|
| ENCODE_ChIP-seq | REST | PFSK-1 |
| ENCODE_ChIP-seq | REST | SK-N-SH |
| ENCODE_ChIP-seq | REST | U87 |
| ENCODE_ChIP-seq | RAD21 | SK-N-SH_RA |
| ENCODE_DNase-seq | DNase | Cerebellum_OC |
| ENCODE_DNase-seq | DNase | SK-N-SH |
| ENCODE_DNase-seq | DNase | Medullo |
| ENCODE_DNase-seq | DNase | Medullo_D341 |
| ENCODE_DNase-seq | DNase | BE2_C |
| ENCODE_DNase-seq | DNase | SK-N-MC |
| ENCODE_DNase-seq | DNase | HA-h |
| ENCODE_DNase-seq | DNase | HAc |
| ENCODE_DNase-seq | DNase | SK-N-SH_RA |
| Roadmapepigenomics_ActiveChromatin | 10_TssBiv | Brain_Germinal_Matrix |
| Roadmapepigenomics_ActiveChromatin | 10_TssBiv | Brain_Inferior_Temporal_Lobe |
| Roadmapepigenomics_ActiveChromatin | 2_TssAFlnk | Neurosphere_Ganglionic_Eminence_Derived |
| Roadmapepigenomics_ActiveChromatin | 10_TssBiv | Brain_Angular_Gyrus |
| Roadmapepigenomics_ActiveChromatin | 10_TssBiv | Brain_Anterior_Caudate |
| Roadmapepigenomics_ActiveChromatin | 10_TssBiv | Brain_Cingulate_Gyrus |
| Roadmapepigenomics_ActiveChromatin | 10_TssBiv | Brain_Dorsolateral_Prefrontal_Cortex |
| Roadmapepigenomics_ActiveChromatin | 2_TssAFlnk | Neurosphere_Cortex_Derived |
| Roadmapepigenomics_ActiveChromatin | 1_TssA | Neurosphere_Ganglionic_Eminence_Derived |
| Roadmapepigenomics_ActiveChromatin | 2_TssAFlnk | Neurosphere_Ganglionic_Eminence_Derived |
| Roadmapepigenomics_HistoneMarks | H3K27me3 | Brain_Germinal_Matrix |
| Roadmapepigenomics_HistoneMarks | H3K27me3 | Brain_Cingulate_Gyrus |
| Roadmapepigenomics_HistoneMarks | H3K4me3 | Brain_Inferior_Temporal_Lobe |
| Roadmapepigenomics_HistoneMarks | H3K4me3 | Neurosphere_Cultured_Cells_Ganglionic_Eminence_Derived |
| Roadmapepigenomics_HistoneMarks | H3K4me3 | Brain_Anterior_Caudate |
| Roadmapepigenomics_HistoneMarks | H3K27ac | Brain_Anterior_Caudate |
| Roadmapepigenomics_HistoneMarks | H3K27me3 | Brain_Hippocampus_Middle |
| Roadmapepigenomics_HistoneMarks | H3K9ac | Brain_Anterior_Caudate |
| Roadmapepigenomics_HistoneMarks | H3K4me3 | Neurosphere_Cultured_Cells_Cortex_Derived |
| Roadmapepigenomics_HistoneMarks | H3K4me3 | Brain_Germinal_Matrix |
| Roadmapepigenomics_HistoneMarks | H3K4me3 | Brain_Angular_Gyrus |
| Roadmapepigenomics_HistoneMarks | H3K27me3 | Brain_Angular_Gyrus |
| Roadmapepigenomics_HistoneMarks | H3K27ac | Brain_Mid_Frontal_Lobe |
| Roadmapepigenomics_HistoneMarks | H3K4me3 | Brain_Cingulate_Gyrus |
| Roadmapepigenomics_HistoneMarks | H3K27me3 | Brain_Mid_Frontal_Lobe |
| Roadmapepigenomics_HistoneMarks | H3K27me3 | Brain_Anterior_Caudate |
| Roadmapepigenomics_HistoneMarks | H3K9ac | Brain_Mid_Frontal_Lobe |

TABLE 5-continued

Findings from evaluation of OPRM1 promoter region using functional genomics datasets in neuronal cell-type

| | | |
|---|---|---|
| Roadmapepigenomics_HistoneMarks | H3K27me3 | Brain_Substantia_Nigra |
| Roadmapepigenomics_HistoneMarks | H3K27ac | Brain_Inferior_Temporal_Lobe |
| Roadmapepigenomics_HistoneMarks | H3K4me3 | Brain_Mid_Frontal_Lobe |
| Roadmapepigenomics_HistoneMarks | H3K27me3 | Brain_Inferior_Temporal_Lobe |
| Roadmapepigenomics_HistoneMarks | H3K9ac | Brain_Cingulate_Gyrus |
| Roadmapepigenomics_HistoneMarks | H3K4me1 | Brain_Angular_Gyrus |
| Roadmapepigenomics_HistoneMarks | H3K9ac | Brain_Angular_Gyrus |
| Roadmapepigenomics_HistoneMarks | H3K4me1 | Neurosphere_Cultured_Cells_Cortex_Derived |
| Roadmapepigenomics_HistoneMarks | H3K9ac | Brain_Inferior_Temporal_Lobe |
| Roadmapepigenomics_HistoneMarks | H3K4me3 | Neurosphere_Cultured_Cells_Cortex_Derived |
| Roadmapepigenomics_HistoneMarks | H3K4me1 | Neurosphere_Cultured_Cells_Ganglionic_Eminence_Derived |
| Roadmapepigenomics_HistoneMarks | H3K27ac | Brain_Mid_Frontal_Lobe |
| UMMSBrain_H3K4me3 | H3K4me3 | Brain_prefrontal_cortex |

| | | Chromosome 6 | |
|---|---|---|---|
| Data set name | Cell-type group | Start | End |
| ENCODE_ChIP-seq | Neuron | 154360476 | 154360892 |
| ENCODE_ChIP-seq | Neuron | 154360476 | 154360892 |
| ENCODE_ChIP-seq | Glial_cell | 154360476 | 154360892 |
| ENCODE_ChIP-seq | Neuron | 154360485 | 154360774 |
| ENCODE_DNase-seq | Cerebellum | 154360055 | 154361686 |
| ENCODE_DNase-seq | Neuron | 154360205 | 154361641 |
| ENCODE_DNase-seq | Neuron | 154360485 | 154360635 |
| ENCODE_DNase-seq | Neuron | 154360500 | 154360704 |
| ENCODE_DNase-seq | Neuroblast | 154360520 | 154360670 |
| ENCODE_DNase-seq | Neuron | 154360560 | 154360710 |
| ENCODE_DNase-seq | Glial_cell | 154360580 | 154360730 |
| ENCODE_DNase-seq | Glial_cell | 154360620 | 154360770 |
| ENCODE_DNase-seq | Neuron | 154360660 | 154360810 |
| Roadmapepigenomics_ActiveChromatin | Germinal_matrix | 154360200 | 154361000 |
| Roadmapepigenomics_ActiveChromatin | Temporal_lobe | 154360200 | 154361000 |
| Roadmapepigenomics_ActiveChromatin | Neurosphere | 154360200 | 154360600 |
| Roadmapepigenomics_ActiveChromatin | Angular_gyrus | 154360400 | 154361200 |
| Roadmapepigenomics_ActiveChromatin | Caudate-putamen | 154360400 | 154361200 |
| Roadmapepigenomics_ActiveChromatin | Cingulate_gyrus | 154360400 | 154361800 |
| Roadmapepigenomics_ActiveChromatin | Prefrontal_cortex | 154360400 | 154361800 |
| Roadmapepigenomics_ActiveChromatin | Neurosphere | 154360400 | 154361000 |
| Roadmapepigenomics_ActiveChromatin | Neurosphere | 154360600 | 154360800 |
| Roadmapepigenomics_ActiveChromatin | Neurosphere | 154360800 | 154361000 |
| Roadmapepigenomics_HistoneMarks | Germinal_matrix | 154359832 | 154361779 |
| Roadmapepigenomics_HistoneMarks | Cingulate_gyrus | 154359959 | 154360615 |
| Roadmapepigenomics_HistoneMarks | Temporal_lobe | 154360134 | 154361957 |
| Roadmapepigenomics_HistoneMarks | Neurosphere | 154360141 | 154361032 |
| Roadmapepigenomics_HistoneMarks | Caudate-putamen | 154360158 | 154361200 |
| Roadmapepigenomics_HistoneMarks | Caudate-putamen | 154360161 | 154361089 |
| Roadmapepigenomics_HistoneMarks | Hippocampus | 154360219 | 154361820 |
| Roadmapepigenomics_HistoneMarks | Caudate-putamen | 154360231 | 154360919 |
| Roadmapepigenomics_HistoneMarks | Neurosphere | 154360232 | 154360613 |
| Roadmapepigenomics_HistoneMarks | Germinal_matrix | 154360236 | 154361028 |
| Roadmapepigenomics_HistoneMarks | Angular_gyrus | 154360273 | 154361216 |
| Roadmapepigenomics_HistoneMarks | Angular_gyrus | 154360276 | 154361392 |
| Roadmapepigenomics_HistoneMarks | Frontal_lobe | 154360280 | 154360645 |
| Roadmapepigenomics_HistoneMarks | Cingulate_gyrus | 154360289 | 154361329 |
| Roadmapepigenomics_HistoneMarks | Frontal_lobe | 154360308 | 154360649 |
| Roadmapepigenomics_HistoneMarks | Caudate-putamen | 154360363 | 154361164 |
| Roadmapepigenomics_HistoneMarks | Frontal_lobe | 154360541 | 154360711 |
| Roadmapepigenomics_HistoneMarks | Substantia_nigra | 154360548 | 154361656 |
| Roadmapepigenomics_HistoneMarks | Temporal_lobe | 154360556 | 154361011 |
| Roadmapepigenomics_HistoneMarks | Frontal_lobe | 154360586 | 154361813 |
| Roadmapepigenomics_HistoneMarks | Temporal_lobe | 154360592 | 154360975 |
| Roadmapepigenomics_HistoneMarks | Cingulate_gyrus | 154360645 | 154360850 |
| Roadmapepigenomics_HistoneMarks | Angular_gyrus | 154360648 | 154360925 |
| Roadmapepigenomics_HistoneMarks | Angular_gyrus | 154360654 | 154360843 |
| Roadmapepigenomics_HistoneMarks | Neurosphere | 154360679 | 154361066 |
| Roadmapepigenomics_HistoneMarks | Temporal_lobe | 154360694 | 154360980 |
| Roadmapepigenomics_HistoneMarks | Neurosphere | 154360717 | 154360925 |

TABLE 5-continued

Findings from evaluation of OPRM1 promoter region using functional genomics datasets in neuronal cell-type

| | | | |
|---|---|---|---|
| Roadmapepigenomics_HistoneMarks | Neurosphere | 154360784 | 154361032 |
| Roadmapepigenomics_HistoneMarks | Frontal_lobe | 154360822 | 154361016 |
| UMMSBrain_H3K4me3 | Prefrontal_cortex | 154360073 | 154362028 |

Notes:
Chromatin-state learning markers based on a Core 15-state model (ChromHMM), which captures key interactions between the core set of five chromatin marks assayed in all epigenomes (H3K4me3, H3K4me1, H3K36me3, H3K27me3, and H3K9me3). H3K4me3, H3K27ac, H3K4me1, and H3K9ac are histone modifications characteristic of actively transcribed promoter regions, while H3K27me3 is involved in repression of transcription.
Abbreviations:
TSS, transcription start site;
1TssA, active TSS;
2TssAFlnk, flanking active TSS;
10TssBiv, bivalent, poised TSS;
11BivFlnk, flanking bivalent TSS enhancer

Discussion

This study finds associations between epigenetics and CPSP in children for the first time and adds to the emerging evidence linking epigenetic mechanisms to the development of chronic pain states (Denk F et al., 2014). Specifically, we found that DNA methylation of certain CpG sites in the OPRM1 promoter region is associated with preoperative, acute postoperative pain, and CPSP following posterior spine fusion in healthy adolescents. DNA methylation was also associated with pain before surgical stimulus and exposure to opioids. These findings allow for prediction of risk for the pain response to surgery, and possible novel mechanisms which could be targeted for prevention and treatment of CPSP.

Endogenous opioid peptides and exogenously administered opioid analgesics bind to MOR to regulate pain responses. The MOR activity is regulated at different levels, including epigenetic mechanisms (Hwang C K et al., 2007). Many of the CpG sites found to be associated with pain outcomes (1, 3, 4, 9, 11, 13, 17, 18 and 22) have been previously described as putative Sp1 transcription factor binding sites. These include CpG sites 9, 10, 12, 16, 21, 22 and 23 at −18, −14, +12, +84, +145, +150 and +159 from ATG site, respectively (Nielsen D A et al., 2009). Methylation levels at some of these sites were previously found to be associated with opioid addiction/dependence. Nielsen et al found that CpG sites at −18 and +84 (9 and 16) were more strongly methylated in heroin addicts than controls. Similarly, seven CpG sites showed significant hypeimethylation of blood DNA taken from male opioid addicts when compared to blood DNA from controls (CpGs 5, 9, 10, 11, 18, and 23) (Chorbov V M et al., 2011). Increased methylation within the OPRM1 promoter at −14 and −10 from ATG site (CpG 10 and 11)) was also found to be associated with worse neonatal abstinence syndrome outcomes in infants exposed to opioid in utero (Wachman E M et al., 2014).

It has been shown in mouse brain tissues that DNA methylation of the OPRM1 promoter decreases expression of the gene; through interaction with chromatin-remodeling factors, remodeling occurs, thus allowing access for Sp1 binding (Hwang C K et al., 2009), which results in MOR upregulation. Thus, methylation at these sites can prevent the OPRM1 activation, leading to decreased endogenous and exogenous opioid effects, manifested in the experience of increased perioperative pain. In addition, Chorbov et al also observed increased DNA methylation in the speini of addicts, which may suggest a means of epigenetic heritability of opioid phenotypes (Chorbov V M et al, 2011).

Animal studies have shown that OPRM1 promoter methylation reduced OPRM1 expression (Hwang C K et al., 2007). Knothe et al confirmed methylation effects on OPRM1 expression through experiments in human cell lines (neuronal SHSY5Y and Kelly, and non-neuronal HEK-293) with and without the demethylating agent 5'-aza-2'-deoxycytidin (Knothe C et al., 2016). But they did not find that methylation profiles across the OPRM1 gene from CpG position −93 to +159 in brain tissue collected postmortem from heroin addicts correlated with differences in OPRM1 mRNA expression in the corresponding brain regions (Knothe C et al., 2016). Opioid exposure in all their subjects may have played a role in minimizing methylation differences between the specimens, and the individuals. Hence, the lack of correlation in their study does not rule out differences that may exist between opioid-exposed and nonopioid-exposed (or pain versus no pain) subjects.

The findings of this study corroborate a growing body of evidence that OPRM1 DNA methylation affects pain behaviors and contributes to the limited efficacy of opiates in certain cases (Porreca F et al, 1998), which is improved upon blockade of methylation (Viet C T et al., 2014). In a neuropathic animal model, it was shown that increased methylation of the MOR gene proximal promoter in dorsal root ganglion decreased morphine analgesia (Zhou X L et al, 2014). Administration of demethylating agents reversed the hypeimethylation of the OPRM1 gene and improved the analgesic effect of morphine in mice pain models (Zhou X L et al, 2014; Sun Y et al., 2015). It is not clear if pain is the trigger or the consequence of increased methylation of the OPRM1 promoter. In fact, chronic opioid use in methadone-substituted former opiate addicts was found to be associated with increased DNA methylation at OPRM1 position +126 (CpG 18), correlating with increased pain, compared to controls with pain not treated with opioids (Doehring A et al, 2013). The authors note that causal relationships with opioid use could not be established, as there was no opioid dose dependency. In their discussion, they mentioned that the trigger for increased methylation may actually be the baseline increased pain (Denk F et al., 2012). This might partly explain the association of OPRM1 methylation with baseline pain identified in our study, as MOR function is essential for endogenous opioid action even in the absence of opioids. Useful information would be gained by evaluating DNA methylation changes over time in those who do and do not develop CPSP, in the presence/absence of opioids.

Although the exact mechanisms by which DNA methylation of OPRM1 promoter region contributes to pain are not known, the computational analysis revealed a DNA region bound by the repressor element 1 silencing transcription factor (REST) in multiple neuronal cell lines at the OPRM1 promoter region (Table 5). Intriguingly, REST has previously been implicated in OPRM1 gene silencing via epigenetic modifications (Formisano L et al., 2007). REST, a member of the zinc finger transcription factor family, represses transcription of neural genes (Bruce A W et al., 2004) in non-neuronal cells by binding a DNA sequence element called the neuron-restrictive silencer element (NRSE) (Schoenherr C J et al., 1995) and recruiting several chromatin-modifying enzymes (Buckley N J et al, 2010). There is also evidence for the involvement of REST in chronic neuropathy (Formisano L et al., 2007). Nerve injury results in a long-lasting increase in REST expression in mouse dorsal root ganglia (Uchida H et al., 2010).

Hence, it is hypothesized that, in patients with already suppressed OPRM1 expression due to DNA methylation of the OPRM1 promoter, increased REST expression after injury possibly leads to further OPRM1 gene silencing and worsens the pain experience. If true, this mechanism could potentially create new avenues for pain therapy. Besides the sequence specific REST, RAD21 was another transcription factor that was found to be relevant in neuronal cells for the OPRM1 promoter region. REST is involved in three-dimensional DNA organization. Recent research using ChIP-seq and RNA-seq data from matching cell types from the human ENCODE resource, showed that RAD21 mostly functions as an activator of transcription (Banks C J et al., 2016). Although not known to play a role in OPRM1 regulation or pain, DNA methylation preventing binding of an activating transcription factor may also be responsible for the decreased function of OPRM1 and hence increased pain in these patients.

In summary, we report novel associations of DNA methylation in the OPRM1 promoter with preoperative, acute and chronic post-surgical pain in children undergoing spine surgery. Since DNA methylation is influenced by multiple modifiable factors (diet, exercise, parental upbringing, stress), understanding the role of epigenetic regulation of OPRM1 in pain opens new avenues of pain research. Understanding susceptibility may act as a guide for targeted use of aggressive multimodal analgesia, use of calcium-channel modulators (like gabapentin) and preemptive analgesics like N-methyl-D-aspartate receptor antagonists (like ketamine), regional anesthesia, and behavioral therapies in patients with higher risk. Addressing this higher risk using alternative strategies (Kieffer B L et al., 2004) This may be especially important as the MOR protein encoded by OPRM1 plays a key role in mediating not only pain responses but also the development of tolerance and physical dependence (Law P Y et al., 2004). Future studies need to map methylation changes in the OPRM1 promoter over the time course of CPSP, and the effect of preventive and therapeutic strategies on transition of acute pain to CPSP, and development of tolerance/opioid hyperalgesia.

Equivalents

Those skilled in the art will recognize or be able to ascertain using no more than routine experimentation, many equivalents to the specific embodiments of the invention as described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method for mitigating an atypical opioid response manifesting as perioperative pain in a human subject in need thereof, the method comprising
assaying, in vitro, a biological sample from a subject to determine a methylation status of at least one CpG site in the human mu-1 opioid receptor gene (OPRM1), wherein the at least one CpG site in OPRM1 is selected from the group consisting of CpG sites 1, 3, 4, 9, 11, 13, 17, and 22 as defined in Table 4,
identifying the subject in need thereof as one who is susceptible to the atypical opioid response where the susceptible subject has a methylation status of "methylated" at the at least one CpG site, and
administering to the susceptible subject identified as susceptible to the atypical opioid response a demethylating agent, an inhibitor of the repressor element-1 silencing transcription factor (REST) and/or a regimen of multimodal analgesia for perioperative pain management, thereby mitigating the atypical opioid response in the susceptible subject.

2. The method of claim 1, wherein the perioperative pain is selected from the group consisting of preoperative pain, acute postoperative pain, and chronic postoperative pain.

3. The method of claim 2, wherein the perioperative pain is chronic postoperative pain.

4. The method of claim 3, wherein the at least one CpG site is selected from the group consisting of CpG sites 13 and 22 as defined in Table 4.

5. The method of claim 1, wherein the biological sample is a blood sample.

6. The method of claim 1, wherein the atypical opioid response is selected from the group consisting of opioid tolerance and hyperalgesia.

7. The method of claim 1, wherein the demethylating agent or REST inhibitor is administered before or after a surgical procedure is performed on the susceptible subject.

8. The method of claim 7, wherein the demethylating agent is selected from the group consisting of procaine, zebularine, decitabine, and combinations thereof.

9. The method of claim 8, wherein the demethylating agent is zebularine, decitabine, or a combination thereof.

10. The method of claim 1, wherein the susceptible subject is administered a regimen of multimodal analgesia.

11. The method of claim 10, wherein the regimen of multimodal analgesia comprises administering to the susceptible subject one or more agents selected from the group consisting of acetaminophen, a nonsteroidal anti-inflammatory drug (NSAID), gabapentin, pregabalin, a TRPV1 agonist, an NMDA receptor antagonist, an alpha-2 agonist, a dual acting agent, transdermal fentanyl, a long acting local anesthetic, and a cannabinoid.

12. The method of claim 10, wherein the regimen of multimodal analgesia comprises administering to the susceptible subject one or more agents selected from the group consisting of capsaicin, ketamine, memantine, clonidine, dexmedetomidine, and tapentadol.

13. The method of claim 11, wherein the administering of the one or more agents is before or after a surgical procedure is performed on the susceptible subject.

14. The method of claim 11, wherein the administering of at least one of the one or more agents is after a surgical procedure is performed on the susceptible subject.

15. The method of claim 12, wherein the administering of the one or more agents is before or after a surgical procedure is performed on the susceptible subject.

16. The method of claim 12, wherein the administering of at least one of the one or more agents is after a surgical procedure is performed on the susceptible subject.

17. The method of claim 1, wherein the biological sample is assayed by a method comprising isolation of genomic DNA from the biological sample.

18. The method of claim 1, wherein the biological sample is assayed by a method comprising pyrosequencing.

19. The method of claim 18, wherein the pyrosequencing comprises two or more rounds of a polymerase chain reaction.

20. The method of claim 1, wherein the susceptible subject is a female subject.

21. The method of claim 1, wherein the susceptible subject is self-reported Caucasian or white.

* * * * *